(12) United States Patent
Stobrawa et al.

(10) Patent No.: US 12,076,275 B2
(45) Date of Patent: *Sep. 3, 2024

(54) DEVICE AND METHOD FOR PRODUCING CONTROL DATA FOR THE SURGICAL CORRECTION OF THE DEFECTIVE EYE VISION

(71) Applicant: Carl Zeiss Meditec AG, Jena (DE)

(72) Inventors: Gregor Stobrawa, Jena (DE); Mark Bischoff, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 377 days.

This patent is subject to a terminal disclaimer.

(21) Appl. No.: 17/091,960

(22) Filed: Nov. 6, 2020

(65) Prior Publication Data
US 2021/0121323 A1 Apr. 29, 2021

Related U.S. Application Data

(62) Division of application No. 14/707,578, filed on May 8, 2015, now Pat. No. 10,828,197, which is a division
(Continued)

(30) Foreign Application Priority Data
Jan. 21, 2009 (DE) .......................... 102009005482.0

(51) Int. Cl.
*A61F 9/008* (2006.01)
(52) U.S. Cl.
CPC .......... *A61F 9/008* (2013.01); *A61F 9/00827* (2013.01); *A61F 9/00836* (2013.01);
(Continued)
(58) Field of Classification Search
CPC ....................................................... A61F 9/008
(Continued)

(56) References Cited

U.S. PATENT DOCUMENTS 5,549,599 A * 8/1996 Sumiya ............... A61F 9/00804
606/5
5,549,632 A 8/1996 Lai
(Continued)

FOREIGN PATENT DOCUMENTS

DE 695 00 997 T2 4/1998
DE 103 34 110 A1 2/2005
(Continued)

OTHER PUBLICATIONS

Becker et al., "PresbyLASIK-Behandlungsansätze mit dem Eximerlaser", Ophthalmologe (2006), p. 667-672. English Abstract—see p. 669.
(Continued)

*Primary Examiner* — Lynsey C Eiseman
(74) *Attorney, Agent, or Firm* — DeWitt LLP

(57) ABSTRACT

A device for producing control data for a laser device for the surgical correction of defective vision. The device produces the control data such that the laser emits the laser radiation such that a volume in the cornea is isolated. The device calculates a radius of curvature $R_{CV}^*$ to determine the control data, the cornea reduced by the volume having the radius of curvature $R_{CV}^*$ and the radius of curvature being site-specific and satisfying the following equation: $R_{CV}^*(r, \varphi) = 1/((1/R_{CV}(r,\varphi)) + B_{COR}(r,\varphi)/(n_c-1)) + F$, wherein $R_{CV}(r,\varphi)$ is the local radius of curvature of the cornea before the volume is removed, $n_c$ is the refractive index of the material of the cornea, F is a coefficient, and $B_{COR}(r,\varphi)$ is the local change in refractive force required for the desired correction of defective vision in a plane lying in the vertex of the cornea, and at least two radii r1 and r2 satisfy the equation $B_{COR}(r=r1,\varphi) \neq B_{COR}(r=r2,\varphi)$.

17 Claims, 10 Drawing Sheets

Related U.S. Application Data of application No. 13/145,761, filed as application No. PCT/EP2010/050700 on Jan. 21, 2010, now Pat. No. 9,050,172.

(52) U.S. Cl.
CPC ....... *A61F 9/00829* (2013.01); *A61F 9/00838* (2013.01); *A61F 2009/00872* (2013.01); *A61F 2009/0088* (2013.01); *A61F 2009/00882* (2013.01)

(58) Field of Classification Search
USPC ......................................................... 606/4–6
See application file for complete search history.

(56) References Cited

U.S. PATENT DOCUMENTS

| | | | |
|---|---|---|---|
| 5,656,186 | A | 8/1997 | Mourou et al. |
| 5,906,608 | A * | 5/1999 | Sumiya ............... A61F 9/00817 606/4 |
| 5,907,388 | A | 5/1999 | Fujieda |
| 5,993,438 | A | 11/1999 | Juhasz et al. |
| 6,033,075 | A * | 3/2000 | Fujieda .................. A61B 3/107 351/212 |
| 6,110,166 | A | 8/2000 | Juhasz |
| 6,467,907 | B1 * | 10/2002 | Fujieda .................. A61B 3/103 351/212 |
| 6,585,723 | B1 * | 7/2003 | Sumiya ............... A61F 9/00804 606/5 |
| 6,648,877 | B1 | 11/2003 | Juhasz |
| 7,131,968 | B2 | 11/2006 | Bendett et al. |
| 2001/0010003 | A1 | 7/2001 | Lai |
| 2002/0040219 | A1 | 4/2002 | Nakamura et al. |
| 2003/0212387 | A1 | 11/2003 | Kurtz et al. |
| 2004/0070761 | A1 | 4/2004 | Horvath et al. |
| 2004/0169820 | A1 | 9/2004 | Dai et al. |
| 2005/0107775 | A1 | 5/2005 | Huang et al. |
| 2005/0270491 | A1 | 12/2005 | Dai et al. |
| 2007/0179483 | A1 | 8/2007 | Muhlhoff et al. |
| 2007/0293851 | A1 | 12/2007 | Muhlhoff et al. |
| 2008/0021443 | A1 | 1/2008 | Bischoff et al. |
| 2008/0195086 | A1 | 8/2008 | Schroeder et al. |
| 2008/0223707 | A1 | 9/2008 | Muehlhoff et al. |
| 2008/0252848 | A1 | 10/2008 | Dai |
| 2008/0319428 | A1 | 12/2008 | Wiechmann et al. |
| 2010/0331830 | A1 | 12/2010 | Bischoff et al. |
| 2010/0331831 | A1 | 12/2010 | Bischoff et al. |
| 2011/0034911 | A1 | 2/2011 | Bischoff et al. |

FOREIGN PATENT DOCUMENTS

| | | |
|---|---|---|
| DE | 103 58 927 A1 | 7/2005 |
| DE | 10 2005 013 558 A1 | 9/2006 |
| DE | 10 2006 053 118 A1 | 5/2008 |
| DE | 10 2006 053 119 A1 | 5/2008 |
| DE | 10 2006 053 120 A1 | 5/2008 |
| DE | 10 2007 053 281 A1 | 5/2009 |
| DE | 10 2007 053 283 A1 | 5/2009 |
| DE | 10 2008 017 293 A1 | 10/2009 |
| EP | 1 153 584 A1 | 11/2001 |
| EP | 1 159 986 A2 | 12/2001 |
| WO | WO 96/11655 | 4/1996 |
| WO | WO 2004/032810 A2 | 4/2004 |
| WO | WO 2005/011546 A1 | 2/2005 |
| WO | WO 2005/011547 A1 | 2/2005 |
| WO | WO 2005/092172 A1 | 10/2005 |
| WO | WO 2007/022993 A2 | 3/2007 |
| WO | WO 2008/055697 A1 | 5/2008 |
| WO | WO 2008/055705 A1 | 5/2008 |
| WO | WO 2009/124668 A2 | 10/2009 |

OTHER PUBLICATIONS

Chang et al., "Corneal Tissue Ablation Depth and the Munnerlyn Formula", J. Cataract Refract Surg (2003), vol. 29, p. 1204-1210.

Application and File History for U.S. Appl. No. 13/145,761, filed Oct. 5, 2011. Inventors: Gregor Stobrawa et al.

Application and File History for U.S. Appl. No. 14/707,578, filed May 8, 2015. Inventors: Gregor Stobrawa et al.

* cited by examiner

FIG 4
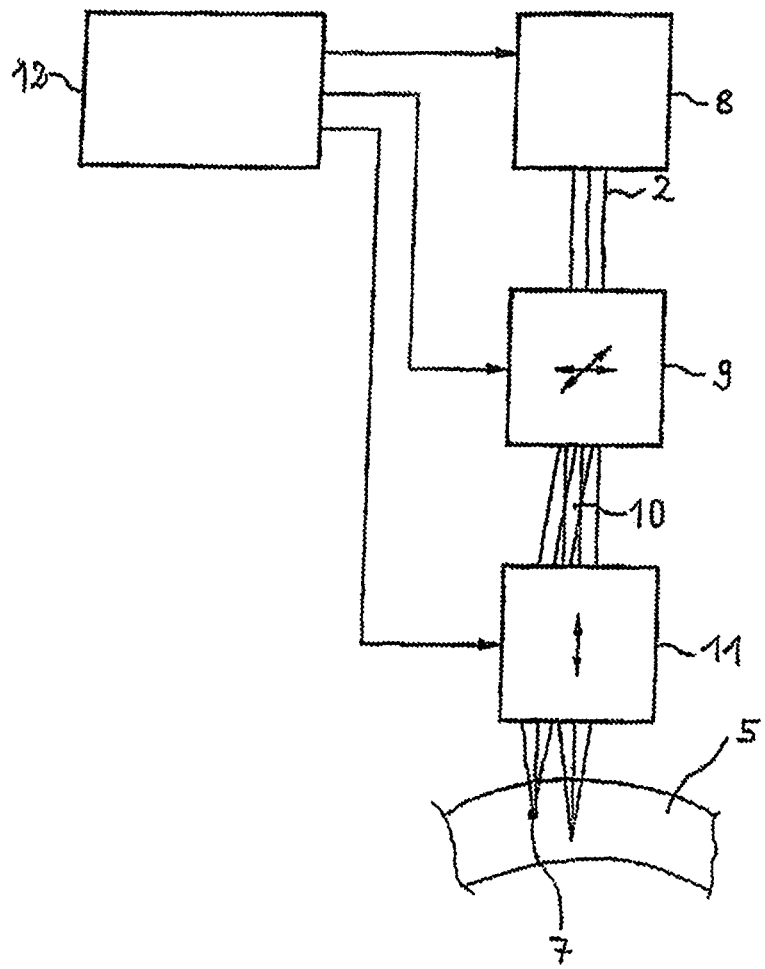
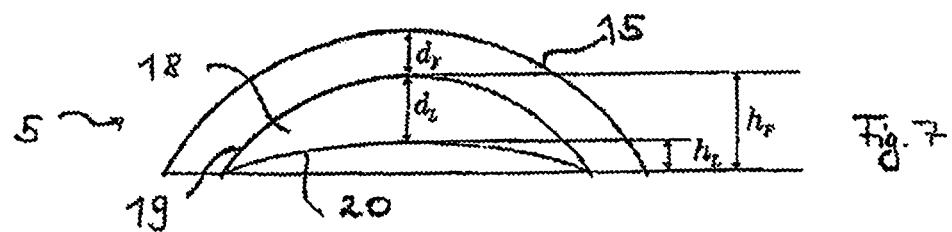
Fig. 7

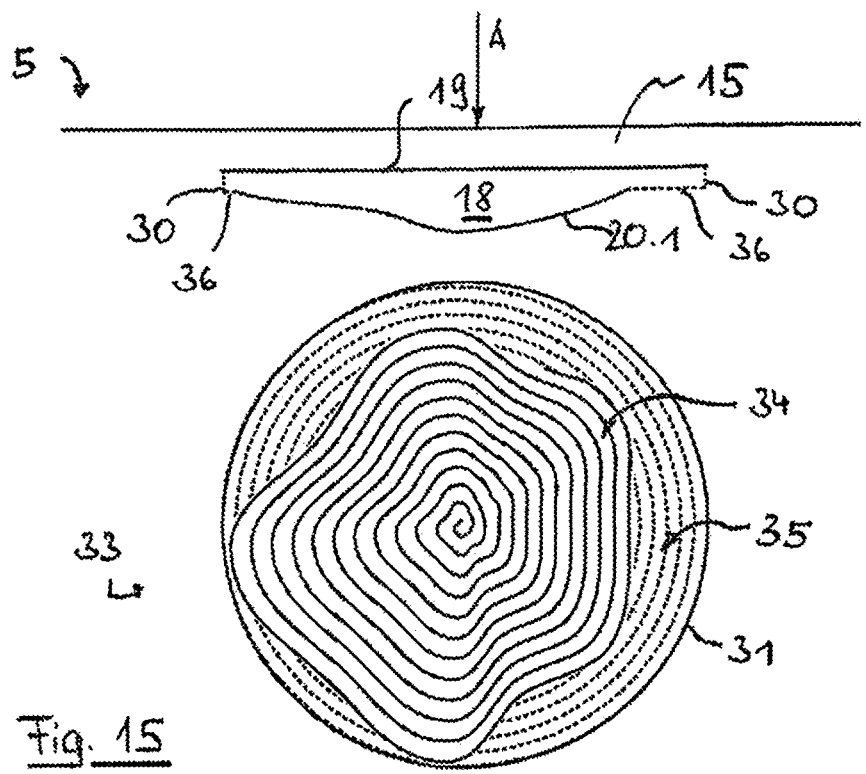
Fig. 15
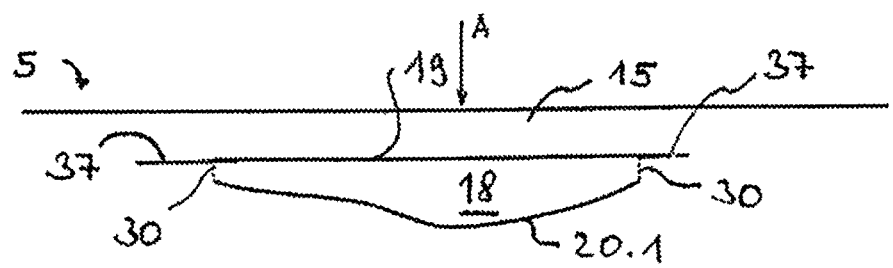
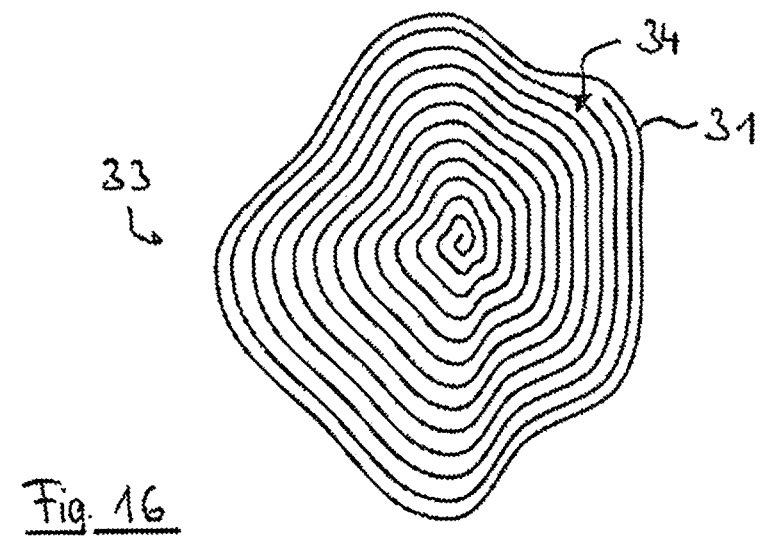
Fig. 16

DEVICE AND METHOD FOR PRODUCING CONTROL DATA FOR THE SURGICAL CORRECTION OF THE DEFECTIVE EYE VISION

PRIORITY CLAIM

This application is a divisional of application Ser. No. 14/707,578 filed May 8, 2015 entitled "Device and Method for Producing Control Data for the Surgical Correction of the Defective Vision of an Eye" which is a divisional of application Ser. No. 13/145,761 filed Oct. 5, 2011 entitled "Device and Method for Producing Control Data for the Surgical Correction of the Defective Vision of an Eye", now U.S. Pat. No. 9,050,172, issued Jun. 9, 2015, which is a National Phase entry of PCT Application No. PCT/EP2010/050700, filed Jan. 21, 2010, which claims priority from German Application Number 102009005482.0, filed Jan. 21, 2009, the disclosures of which are hereby incorporated by reference herein in their entirety.

FIELD OF THE INVENTION

In a first variant the invention relates to a device for generating control data for controlling a laser for the surgical correction of the defective vision of an eye of a patient, wherein the control data are adapted to control a laser which cuts cornea tissue by irradiating laser radiation into the cornea of the eye, the device generates the control data such that the laser, during operation according to the control data, emits the laser radiation such that a volume in the cornea is isolated, the removal of which from the cornea effects the desired correction of defective vision and, to determine the control data, the device calculates a radius of curvature that the cornea has when reduced by the volume.

In the first variant the invention further relates to a method for generating control data for controlling a laser for the surgical correction of the defective vision of an eye of a patient, wherein the control data are adapted to control a laser which cuts cornea tissue by irradiating laser radiation into the cornea of the eye, the control data are generated such that the laser, during operation according to the control data, emits the laser radiation such that a volume in the cornea is isolated, the removal of which from the cornea effects the desired correction of defective vision and, to determine the control data, a radius of curvature that the cornea has when reduced by the volume is calculated.

In a second variant the invention relates to a method for generating control data which are adapted to control a laser treatment device for the surgical correction of defective vision of an eye of a patient, wherein a correction surface is predetermined which is to be produced in the cornea for the removal of a volume and which is non-rotation-symmetrical relative to a main direction of incidence, and wherein in the method the control data are generated on basis of the correction surface such that, during operation, the laser treatment device produces the correction surface as a cut surface in the cornea, and the non-rotation-symmetrical correction surface is adapted to a contour that is circular when viewed in the main direction of incidence of the laser radiation.

BACKGROUND

In the second variant the invention further relates to a device for generating control data which are adapted to control a laser treatment device for surgical correction of defective vision of an eye of a patient, wherein a correction surface is predetermined which is to be produced as cut surface in the cornea for the removal of a volume and which is non-rotation-symmetrical relative to a main direction of incidence, and wherein the device generates the control data on basis of the correction surface such that, during operation, the laser treatment device produces the correction surface in the cornea and that, during generating of the control data, the device adapts the non-rotation-symmetrical correction surface to a contour that is circular when viewed in the main direction of incidence of the laser radiation.

Spectacles are the traditional way of correcting defective vision in the human eye. However, refractive surgery which corrects defective vision by altering the cornea is now also increasingly being used. The aim of the surgical methods is to selectively alter the cornea so as to influence refraction. Differing procedures of surgeries are known for this purpose. Currently the most widespread is the so-called laser-assisted in situ keratomileusis, also abbreviated to LASIK. Firstly, a lamella of the cornea is cut on one side from the cornea surface and folded to the side. This lamella can be cut by means of a mechanical microkeratome or also by means of a so-called laser keratome, such as is marketed e.g. by Intralase Corp., Irvine, USA. After the lamella has been cut and folded to the side, the LASIK operation uses an excimer laser, which removes the thus-exposed corneal tissue by ablation. After volume in the cornea has been vaporized in this manner the lamella of the cornea is folded back into its original place.

The use of a laser keratome to expose the lamella is advantageous as the danger of infection is thereby reduced and the cut quality increased. In particular the lamella can be produced with a very much more consistent thickness. The cut is also potentially smoother, which reduces sight problems due to this boundary surface which remains even after the operation. To produce the cut, a series of incisions of the eye are made at predetermined points such that the cut surface is formed as a result. With the laser keratome the cut surface forms the lamella to be folded back before the use of laser ablation.

With the conventional LASIK method exposed corneal tissue is vaporized, which is also called "grinding" of the cornea by means of laser radiation. The volume removal which is necessary to correct defective vision is set for each surface element of the exposed cornea by the number of laser pulses and their energy. Therefore, in the LASIK method, a so-called shot file is provided for the ablation laser which defines, for different points on the cornea, how often, and with what energy, the laser beam is to be directed onto defined points on the cornea. The volume removal is heuristically determined, not least because it depends greatly on the ablation effect of the laser beam, therefore on the wavelength, fluence etc. of the radiation used. The state of the cornea also plays a role; in particular the moisture content of the cornea is to be mentioned here. WO 96/11655 describes a device and a process for the LASIK method. In particular a formula is given which calculates the radius of curvature to be achieved from the pre-operative radius of curvature of the cornea and the desired diopter correction. A similar calculation is described in EP 1153584 A1—also for corneal ablation by means of LASIK.

U.S. Pat. No. 5,993,438 proposes the removal of a volume from the cornea by vaporization and absorption in the cornea.

WO 2005/092172 discloses how optical refraction power measurements which have been determined in one plane can be transferred into another plane. The document mentions that this process can be used for different eye treatments, in particular for laser-supported ablation.

A further laser-based eye surgery method is not to vaporize the volume to be removed from the cornea, but to isolate it by a laser cut. The volume is thus no longer ablated, but isolated in the cornea by a three-dimensional cut surface and thus made removable. Empirical values which have been developed for grinding the cornea by means of ablation laser radiation cannot be used for such methods. Instead, control data are required to operate the laser for isolating the volume to be removed from the cornea. One such procedure for eye surgery is described in U.S. Pat. Nos. 6,110,166 and 7,131,968. Different volume forms are shown in U.S. Pat. No. 6,110,166 and it is mentioned that the proper volume can be chosen by a person skilled in the art.

DE 102006053118 A1 describes the production of control data for the volume-isolating correction of defective vision.

It is known from DE 102006053120 A1 and DE 102006053119 A1 from Carl Zeiss Meditec A G to base the production of such defective vision on data which give the optical refraction power of spectacles suitable for correcting defective vision. It is also known from this published document, which thus describes a method of the mentioned type and a device of the mentioned type, to use data which also bring about a correction of an astigmatism or corrections of higher-order aberrations. By using data for defective vision which are intended for a conventional spectacle correction, the approach known from DE 102006053120 A1 achieves a considerable simplification in pre-operative eye measurement, as the production of spectacle correction data is daily practice in ophthalmology. However, this simplification also means a degree of limitation of the possible correction results, because inevitably only corrections which would also be possible with normal spectacles can be achieved. It is also to be taken into account here that corrections such as are possible e.g. with varifocals are ruled out for the approach according to DE 102006053120 A1 as such corrections always assume that, depending on the viewing direction, the axis of vision passes through the spectacle lens at different points, which makes it possible to be able to bring different optical properties of the spectacles to bear for different viewing directions (e.g. reading directed more downwards, or viewing directed more into the distance). This does not apply in the case of refractive surgery on the cornea because movement of the eye obviously causes the cornea to move as well when the direction of viewing changes. Thus, unlike with a spectacle lens, there is no change in the point where the optical axis penetrates the cornea when the eyeball rotates. The approach known from DE 102006053120 A1 can thus consequently use only comparatively simple spectacle defective-vision correction data as an input variable for control data, with the consequence of correspondingly limited possibilities of correction.

It is known from DE 10334110 A1 from Carl Zeiss Meditec A G to produce a cut surface which at least partly circumscribes the volume to be removed in order to correct defective vision by shifting the focus of the laser radiation along orbits following contour lines or along a spiral which is based on such contour lines. The planes in which the contour lines are defined or on the basis of which the spiral is defined are oriented perpendicular to the main direction of incidence of the treatment laser radiation. Shifting the focus along the optical axis, which is customarily undertaken by an adjustable zoom lens or similar, thus has the smallest possible restriction on the speed of shifting along the path. As this shift of the focus is generally much slower than the deflection across the main direction of incidence of the treatment laser radiation, the result is a rapid production of the cut surface.

This publication describes that corrections of defective vision which go beyond a spherical correction, for example to correct an astigmatism, consistently require aspherical cut surfaces, for example cut surfaces in the form of an ellipsoid. In this connection DE 10334110 A1 describes that such a cut surface can be given a circular contour as seen along the main direction of incidence if the operating laser radiation is deactivated in sections which go beyond such a circular contour. FIG. 11 shows the conditions obtained in this case. A sectional representation through a cornea 5 in which a volume 18 is isolated and prepared for removal is shown. The volume 18 is defined by an anterior cut surface (flap surface 19) produced substantially parallel to the cornea front surface and a posterior cut surface (lenticle surface 20). A top view 33 of the lenticle surface 20 is shown at the bottom of FIG. 11. It determines the curvature the front of the cornea 15 has once the volume 18 is removed. FIG. 11 shows a case in which an astigmatic correction is to be undertaken, which is why the lenticle surface 20 is an ellipsoid. At the top of FIG. 11, therefore, two cut lines 20.1 and 20.2 which correspond to the main axes H1 and H2 of the ellipsoid surface, are shown for the cut surface 20. In the top view 33 the volume 18 has a circular contour. Furthermore, the ellipsoidal lenticle surface 20 is produced by a spiral-shaped path 32 along which the position of the focus of the treatment laser radiation is shifted, on which thus lie the centers of the laser pulses which produce the processing effect in the cornea 5. In order to achieve a circular contour of the lenticle surface 20, in areas of the spiral 32 which lie outside the circular contour the treatment laser radiation is blanked, i.e. modified such that no processing effects occur there. The connection between the lenticle surface 20 and the flap surface 19 can then be produced by a simple lenticle edge surface 30 in the shape of a circle cone envelope. In the top view 33 of the lenticle surface 20 this is illustrated by a cross-hatched lenticle edge zone 31 which penetrates deeply enough into the cornea for the overall volume 18 to be isolated by the flap surface 19, the lenticle surface 20 and the lenticle edge surface 30.

SUMMARY OF THE INVENTION

The invention thus relates to the concept of carrying out a correction of the optical imaging errors of the human eye by cutting, by means of laser radiation within the cornea, a volume of tissue which is then removed from the cornea. A selective change of the optical refraction power of the cornea is thereby achieved. This change is localized, i.e. in the area of the cornea from which the tissue volume is removed. The pupil of the eye is usually taken as a basis.

The removal of the cut volume changes the geometry, i.e. the curvature of the cornea surface. In order that a desired correction of defective vision is achieved, the cut volume to be removed must therefore have special properties with regard to its shape.

The cut volume is usually circumscribed by three boundary surfaces, based on classic LASIK methods. An anterior boundary surface is formed at a constant distance under the cornea. This is particularly simple if the cornea is flattened by a flat contact glass. As this cut surface directionally lies furthest forward it is called anterior surface or, on the basis of the known LASIK methods, flap surface.

Furthermore, the volume is limited by a deeper-lying cut surface which is called posterior cut surface or, because the volume can be seen as a lenticle, as lenticle surface. Therefore, it is ensured that overall the volume to be removed changes the curvature of the cornea front surface. One of the two surfaces, usually the posterior, generally has a geometry which is decisive for correcting defective vision.

In principle, it could be conceived to design the anterior and posterior surfaces such that they have a common cutting line. Firstly, this is not possible when correcting long-sightedness as there the volume to be removed must be thinner in the centre, i.e. in the area of the axis of vision, than at the edge. Secondly, when correcting farsightedness it might also be wished, for operational reasons, to ensure a certain minimum thickness of the volume at the edge in order to be able to remove it easily. The anterior surface and the posterior surface are therefore connected via a so-called lenticle edge surface.

The cut volume is made removable by these three cut surfaces, as the volume is then completely or almost completely enclosed by the cut surfaces. The absolute position and relative extent of the surfaces in the cornea fix the zone within which the optical effect occurs after removal of the cut volume between these surfaces. Here, as already mentioned, the pupil of the eye is usually taken as basis. This approach leads to both cut surfaces, namely the anterior and posterior cut surface, of which one or both can be optically effective, having to be connected to a closed volume which must have a suitable position within the cornea. As there are also restrictions in terms of equipment for example the possible degrees of freedom of the laser beam deflections, and also application-related requirements, such as for example regression effects in the course of healing, surgical handling properties of the volume of tissue to be removed, maximum tolerable duration for the production of the cut surfaces, etc., overall the resulting edge value problem gets decidedly complex.

The object of the first variant of the invention is to develop a device of the mentioned type or a method of the mentioned type to the effect that control data can be produced for the surgical correction of defective vision with as little computation as possible, and simultaneously, more complex corrections can also be achieved.

This object is achieved according to the invention in the first variant with a device of the type named at the outset in which the radius of curvature $R_{CV}^*$ varies locally and satisfies the following equation:

$$R_{CV}^*(r,\varphi)=1/((1/R_{CV}(r,\varphi))+B_{COR}(r,\varphi)/(n_c-1))+F,$$

wherein $R_{CV}(r,\varphi)$ is the local radius of curvature of the cornea before the volume is removed, ne is the refractive index of the material of the cornea, F is a coefficient, and $B_{COR}(r,\varphi)$ is the local change in optical refraction power required for the desired correction of defective vision in a plane lying in the vertex of the cornea, wherein there are at least two radii, r1 and r2, for which $B_{COR}(r=r1,\varphi) \neq B_{COR}(r=r2,\varphi)$ holds true.

This object is further achieved according to the invention in the first variant with a method for generating control data for a laser of the type named at the outset, wherein the radius of curvature $R_{CV}^*$ varies locally and satisfies the following equation:

$$R_{CV}^*(r,\varphi)=1/((1/R_{CV}(r,\varphi))+B_{COR}(r,\varphi)/(n_c-1))+F,$$

wherein $R_{CV}(r,\varphi)$ is the local radius of curvature of the cornea before the volume is removed, no is the refractive index of the material of the cornea, F is a coefficient, and $B_{COR}(r,\varphi)$ is the local change in optical refraction power required for the desired correction of defective vision in a plane lying in the vertex of the cornea, wherein there are at least two radii, r1 and r2, for which $B_{COR}(r=r1,\varphi) \neq B_{COR}(r=r2,\varphi)$ holds true.

In the first variant, the invention thus provides a control variable or a reference variable on the basis of which the volume to be removed and thus the cut surface isolating this volume in the cornea can be calculated as precisely as possible. It defines an equation for the radius of curvature which the cornea is to have after the removal of the volume isolated by the treatment device or the method. The volume to be removed, and in particular the correction-effective surface, can be calculated in an analytically precise manner with this equation.

Upon closer inspection the equation used according to the invention in the first variant to calculate the volume to be removed differs substantially from the approach such as was used in DE 102006053120 A1. A different function is used which no longer takes into account the optical refraction power of spectacles which lie at a distance to the eye, but a distribution of optical refraction power which, written in circular coordinates, varies at least radially. Additionally, this distribution of optical refraction power with which the new radius of curvature which the cornea must have after the surgical correction is calculated no longer lies at a distance from the cornea, but gives the need for correction in a plane which lies in the vertex of the cornea. The invention adopts the analytical approach of DE 102006053120 A1 and simultaneously abandons the spectacle-correction values used there, introducing a radially varying distribution of optical refraction power which reproduces the need for correction of the plane lying in the vertex of the cornea.

Thus, without the calculation effort being significantly increased, a much more extensive correction of defective vision is possible. For example, a correction value which corresponds to the previous spectacle-correction value can now be applied in a central area about the optical axis, e.g. in the radius of the phototopic pupil and other optical refraction power values can be used for greater diameters. Thus a presbyopia of the eye can be dealt with by carrying out in the central area, i.e. in the radius of the phototopic pupil, a correction of near vision (comparable with reading spectacles) and a correction of distant vision (comparable with distance spectacles).

The volume or the geometry of the correction-effective surface is now determined or can now be determined according to the invention via the equation such that the cornea has the defined radius of curvature after removal of the volume.

A particularly easily calculable and above all also simply achievable (but by no means the only) definition of the volume, limits the volume without restriction to the first variant, by a boundary surface which is divided into an anterior and a posterior surface part (flap surface and lenticle surface), wherein the anterior surface part lies at a constant distance $d_F$ from the cornea front surface. The terms "anterior" and "posterior" correspond to the usual medical nomenclature. An additional edge surface may be necessary (when correcting farsightedness) or advantageous in order to connect the two surface parts and simultaneously guarantee a minimum edge thickness.

Because the anterior surface part (flap surface) is at a constant distance from the cornea surface the formation of this surface part is particularly simple. Naturally, the posterior surface part (lenticle surface) is then not necessarily at a constant distance from the cornea front surface. The optical correction takes place by shaping the posterior surface part (lenticle surface). Calculation effort is considerably simplified by this approach, as a spherical surface part (the anterior surface part) is particularly simple to calculate and the calculation effort is concentrated on the determination of the posterior surface part (lenticle surface). With such an approach, the posterior surface part (lenticle surface) has a curvature pattern which can be identical, apart from an additive constant, to that of the cornea front surface after removal of the volume. The distance between the anterior surface part (flap surface) and the cornea front surface is reflected in the constant.

The radial dependency, present according to the invention in the first variant, of the distribution of optical refraction power means that, viewed in polar coordinates, there are at least two radii for all angles in which there are different values for the distribution of optical refraction power.

The distribution of optical refraction power used may be present as a result of a calculation using wave-front measurement or topography measurement of the cornea front of the cornea. Accordingly, the equation according to the invention on which the calculation of the volume of the cornea is based also provides a local radius of curvature of the cornea. The coordinates system chosen is preferably referenced to the vertex of the cornea.

If the topography $Z_{CV}:R^2 \rightarrow R^3$ (quantity of all points $Z_{CV}(r,\varphi)$ which lie on the front of the cornea) is known the local radius of curvature $R_{CV}(z(r,\varphi))$ can be determined for example by a best matching of a sphere surface with the radius R to the surface $Z_{CV}$ in an infinitesimal radius about the point $z_{CV}(r,\varphi)$. The fitting of a curvature circle in radial direction alone can also be used. Then:

$$R_{CV}(r, \varphi) = \frac{\sqrt{1 + \left(\frac{\partial}{\partial r} z_{CV}(r, \varphi)\right)^2}}{\left|\frac{\partial^2}{\partial r^2} z_{CV}(r, \varphi)\right|}$$

In this way the desired distribution of the radius of curvature of the front of the cornea $R_{CV}^*(r, \varphi)$, which is to be achieved by the refraction correction $B_{COR}(r, \varphi)$ is obtained by means of the equation according to the invention.

The thickness profile $\Delta z(r,\varphi)$ of the volume to be removed is determined or can be determined according to the invention by the topography $z_{CV}^*(r,\varphi)$ of the cornea after the removal of the volume having the local radius of curvature $R_{CV}^*(r,\varphi)$ then:

$$z_{CV}^*(r,\varphi) = z_{CV}(r,\varphi) - \Delta z(r,\varphi).$$

If an isolated volume is removed from the cornea $\Delta z(r,\varphi)$ is always positive. However, this is not a binding condition for the correction. It is likewise possible to change the refractive correction and, associated with this, the radius of the cornea front side by introducing an additional volume into the cornea. In this case $\Delta z(r,\varphi)$ is always negative. Mixed cases are also possible in which $\Delta z(r,\varphi)$ has both positive and negative areas. In practice this is the case if for example a small refractive correction for distant vision in cases of myopia is to be effected by extraction of tissue and simultaneously a correction of presbyopia by implantation of a small lens in the central area of the optical zone. In this case the thickness of the implant may definitely be greater than the thickness of the volume of tissue to be removed for correcting myopia and thus $\Delta z(r,\varphi)$ have positive values in the central area and negative values in the edge area.

The thickness profile $\Delta z(r,\varphi)$ of the volume results from the difference in topographies. If the desired topography after the correction $z_{CV}^*(r,\varphi)$ is known the thickness profile is also determined.

A person skilled in the art can now use analysis or suitable arithmetic methods to determine $z_{CV}^*(r,\varphi)$ from $R_{CV}^*(r,\varphi)$ by double integration over the surface. The two integration constants occurring are chosen such that for example the desired treatment diameter for refractive correction forms and simultaneously the volume to be removed is minimized.

Therefore it is preferred in the first variant that, when determining the control data, the device fixes the local change in optical refraction power $B_{COR}(r,\varphi)$ such that there is a characteristic radius $r_{ch}$ for which the radial function of the change in optical refraction power $B_{COR}(r,\varphi)$ is piecewise constant, for which thus $B_{COR}(r<r_{ch},\varphi=\text{const})=B_a \neq B_b=B_{COR}(r>r_{ch},\varphi=\text{const})$.

The distribution of optical refraction power used for correction can, as already mentioned, have different values in specific areas of the pupil, e.g. a central area as well as an edge area, in order to achieve an optical correction which achieves optimum results even with greatly varying sight conditions or is individually best adapted, e.g. in the case of farsightedness in old age (presbyopia).

In particular it is preferred in the first variant that, when determining the control data, the device fixes the local change in optical refraction power $B_{COR}(r,\varphi)$ such that there is a characteristic radius $r_{ch}$ for which the radial function of the change in optical refraction power $B_{COR}(r,\varphi)$ is piecewise constant, for which thus $B_{COR}(r<r_{ch},\varphi=\text{const})=B_a \neq B_b=B_{COR}(r>r_{ch},\varphi=\text{const})$.

There can be a continuous transition between the partly constant values of the changes in optical refraction power. For this version it is therefore expedient in the first variant that, when determining the control data, the device fixes the local change in optical refraction power $B_{COR}(r,\varphi)$ such that there are two radii $r_a$ and $r_b$ for which the radial function of change in optical refraction power $B_{COR}(r,\varphi)$ is piecewise constant, for which thus $B_{COR}(r<r_a,\varphi=\text{const})=B_a \neq B_b=B_{COR}(r>r_b,\varphi=\text{const})$, wherein the radial function of the change in optical refraction power $B_{COR}(r,\varphi)$ passes continuously from $B_a$ to $B_b$ in the transition area between $r_a$ and $r_b$.

The local change in optical refraction power $B_{COR}(r,\varphi)$ can, as special case, have symmetries which make it possible to separate the relationships between coordinates. This makes possible for example the following notations during production of control values:

$B_{COR}(r,\varphi)=B_1(r) \cdot B_2(\varphi)$ (multiplicative separation approach)

$B_{COR}(r,\varphi)=B_1(r)+B_2(\varphi)$ (additive separation approach).

A special case of the separation results if the optical refraction power distribution is not angle-dependent. As this is particularly simple in terms of calculation it is preferred that, when determining the control data, the local change in optical refraction power is or will be fixed in an angle-independent manner.

It is to be pointed out here, basically, that optical refraction power and radius of curvature can be transformed from one into the other by a simple equation. Thus: $B=(n_C-1)/R$, wherein B is the optical refraction power and R the radius allocated to this optical refraction power. Thus, within the framework of the invention, it is possible at any time to switch between radius approach and optical refraction power approach or representation. The equation to be used when determining the control data in optical refraction power representations reads:

$$B_{CV}^*(r,\varphi) = \cfrac{1}{\cfrac{1}{B_{CV}(r,\varphi) + B_{COR}(r,\varphi)} + \cfrac{F}{(n_C - 1)}}$$

When the radius of the cornea surface is mentioned here, the optical refraction power can also be used completely analogously, with the result that here, all statements made in connection with the radius of the cornea surface self-evidently also analogously apply to the representation or approach of the optical refraction power if R is replaced by B according to the named dependency.

The object of the invention, in particular in the second variant, is to configure the definition of the closed volume within the cornea to be as application favorable as possible and in particular to enable the connection of the two optically effective boundary surfaces, namely the anterior and the posterior surface (flap and lenticle surface) such that secondary biophysical and/or medical effects do not disadvantageously affect the intended optical correction effect, wherein at least one of the surfaces is non-rotation-symmetrical.

This object is achieved according to the second variant of the invention by a method for generating control data which are adapted to control a laser treatment device for surgical correction of defective vision of an eye of a patient, wherein a correction surface is predetermined which is to be produced in the cornea for the removal of a volume and which is non-rotation-symmetrical relative to a main direction of incidence, and wherein in the method the control data are generated on the basis of the correction surface such that, during operation, the laser treatment device produces the correction surface in the cornea, and the non-rotation-symmetrical correction surface is adapted to a contour that is circular when viewed in the main direction of incidence of the laser radiation, wherein there is provided for the correction surface a transition area in which it is adapted from the non-rotation-symmetrical form to a rotation-symmetrical edge relative to the main direction of incidence, wherein the rotation-symmetrical edge is circular and lies in a plane which is perpendicular to the main direction of incidence and which, relative to the main direction of incidence, is neither more anterior than a most anterior point nor more posterior than a most posterior point of the correction surface.

This object is further achieved according to the second variant of the invention by a device for generating control data which are adapted to control a laser treatment device for the surgical correction of the defective vision of an eye of a patient, wherein a cut surface is predetermined which is to be produced in the cornea for the removal of a volume and which is non-rotation-symmetrical relative to the main direction of incidence, and wherein the device generates the control data on the basis of the correction surface such that, during operation, the laser treatment device produces the correction surface in the cornea, and during generating the control data the device adapts the non-rotation-symmetrical correction surface to a contour that is circular when viewed when viewed in the main direction of incidence of the laser radiation, wherein the device provides for the cut surface a transition area in which the correction surface is adapted from the non-rotation-symmetrical form to a rotation-symmetrical edge relative to the main direction of incidence, wherein the rotation-symmetrical edge is circular and lies in a plane which is perpendicular to the main direction of incidence and which, relative to the main direction of incidence, is neither more anterior than a most anterior point nor more posterior than a most posterior point of the correction surface, wherein at least one of the two surfaces is non-rotation-symmetrical.

To understand the invention it is essential to distinguish between different surfaces or cut surfaces which confine the volume which must be removed to correct defective vision. The volume is confined by an anterior surface which is called flap surface or anterior surface, on the basis of the known LASIK method. To the rear the volume is confined by a posterior surface or lenticle surface. At least one of these surfaces affects the post-operative curvature of the front of the cornea, i.e. the curvature of the front of the cornea after removal of the volume. In the description given here, for the sake of simplicity, it is assumed that this correction-effective surface is the lenticle surface. However, this shall not be considered a limitation. The correction-effective region of the relevant surface(s) is called correction zone. This correction zone is non-rotation-symmetrical within the framework of this description as higher aberrations, e.g. an astigmatism, are also to be corrected. The correction zone is a part of the correction-effective surface (e.g. the lenticle surface). When calculating the need for correction or before calculating the control data, a correction surface is predetermined for the correction zone. If there is only a single correction-effective surface, the surface geometry of the correction surface is decisive for the surface geometry of the cornea after the surgical procedure.

The correction surface generally has a non-rotation-symmetrical edge, as it is non-rotation-symmetrical. Joining this edge in the surface is a transition zone, which continues the non-rotation-symmetrical edge of the correction surface such that overall the cut surface has a rotation-symmetrical edge. The correction-relevant cut surface (e.g. the lenticle surface) is thus composed of the correction zone, which is predetermined by the correction surface, and the transition zone which extends the correction surface onto a rotation-symmetrical edge.

As a rule, the flap surface and lenticle surface still do not circumscribe a fully confined volume. The lenticle edge surface which connects the rotation-symmetrical edges of the flap surface to the lenticle surface is still missing. As two rotation-symmetrical edges are connected the lenticle edge surface can be designed as circular cylinder jacket surface or circular cone envelope surface.

A correction surface which, as already mentioned, is non-rotation-symmetrical when correcting higher aberrations is predetermined for the correction. Firstly, the adaptation to a rotation-symmetrical edge can take place by completing the correction surface around the transition zone. Secondly, however, it is also possible to modify an edge area of the correction surface, which generally occurs by having only a specific central portion of the actually predetermined correction surface actually in the cut surface and the transition zone then joining onto this portion. Which of the two options is chosen depends exclusively on to what extent the predetermined correction surface covers the desired pupil area. If it is sufficiently larger than the desired pupil area in which the optical correction is to be effective, the second-named option (modifying the edge area of the correction surface) can be chosen. In the other case the transition zone will be joined onto the correction surface. However, from the point of view of the principles described here, there is no substantial difference between these two options.

Nor does it make any difference as to whether a single one correction-effective surface is used, or two. If only one correction-effective surface is used this is usually the lenticle surface, as this is also generally produced first. However, this is not essential. If a single correction-effective surface (e.g. the lenticle surface) is used, the other surface (e.g. the flap surface) must be at a constant distance from the front of the cornea, thus as a rule be rotation-symmetrical, as otherwise it would have a correction-effective property. When there are two correction-effective surfaces, what has been said concerning the embodiment with only one correction-effective surface, with regard to the design of this correction-effective surface, naturally applies equally for both correction-effective surfaces. In other words, both correction-effective surfaces are provided with corresponding transition zones (either by modification or by extending the surface edge) in order to achieve the desired rotation-symmetrical walls for both surfaces.

The invention of the second variant thus provides a transition area (here also called transition zone) which is always attached to the radial limit of the non-rotation-symmetrical surface and continues this onto a rotation-symmetrical edge which, with regard to the axis of main incidence, lies neither higher nor lower than the actual correction surface itself.

As already shown, the refractive correction forms due to the geometry of the anterior cut surface $F_A$ (flap surface) and the posterior cut surface $F_P$ (lenticle surface) of the volume of tissue to be extracted. The shape of the two surfaces $F_A$, $F_P$ is determined by the correction of the local optical refraction power $B(r, \varphi)$ (see e.g. DE 102006053120 A1). The radial (lateral) extents $r_{MAX}(F_A, \varphi)$ and $r_{MAX}(F_P, \varphi)$ of these two surfaces are at least as large as the radius of the correction zone in which the optical refraction power correction shall be effected. The correction zone generally covers the optical zone of the cornea, thus the zone which is pierced by beams of light which then help form display images on the retina. The minimum distance between the two surfaces $F_A$ and $F_P$ along these edge curves $r_{MAX}(F_A, \varphi)$ and $r_{MAX}(F_P, \varphi)$ is generally not constant (see also DE 102007053281 A1).

Attached to the edge curves of the respective non-rotation-symmetrical limit surface $r_{MAX}(F_A, \varphi)$ and/or $r_{MAX}(F_P, \varphi)$ are constant transition areas $ÜZ_A$ and $ÜZ_P$ which then pass into a circular edge. A transition area can also be attached to only one of the two surfaces.

As a result, it is thus ensured that only still rotation-symmetrical edges need be connected by the lenticle edge section. An easily calculable and rapidly producible circular cone or circular cone envelope surface can be used for this.

The transition area can basically be considered for all types of cut surface production. As is explained below, it is particularly expedient to produce the cut surfaces by arranging along a predetermined path a series of laser pulses which are introduced into the cornea. However, this is not necessary; other ways of producing cut surfaces also come into consideration. Subject to the constraint of technically tightly limited speed and acceleration of the z-focus shift of the laser radiation, the so-called contour-line scan method according to WO 002005011547 A1 is suitable for producing any curved cut surfaces by arranging a series of laser pulses along a path.

The transition zone completes the correction surface or adapts it such that it has a rotation-symmetrical edge. This can take place particularly simply by forming the transition area as a flat surface which lies perpendicular to the main direction of incidence, joining onto the edge of the correction surface which is guided as far as the plane in which the flat surface lies and which completes the correction surface onto the circular contour. If the non-rotation-symmetrical edge of the correction surface still does not lie in a plane, in this variant the cut surface is completed until the non-rotation-shaped edge of the correction surface lies in a plane.

In combination with the production of a cut surface in which the focus of the treatment laser radiation is shifted along a path, there are different possibilities for setting the curves of the path, such that adapting the non-rotation-symmetrical edge to the circular contour, thus the transition area, can be defined particularly easily. In a first variant it is provided that the laser treatment device is adapted to focus treatment laser radiation into the cornea of the eye along a main direction of incidence and to shift the position of the laser focus within the cornea, that the rotation-symmetrical edge is fixed, and that the control data are generated such that they define a path along which the laser focus is to be shifted, wherein the path lies in the predetermined correction surface and runs spirally from inside the predetermined correction surface to its edge, wherein the control data continue the spiral in the transition area such that one ach revolution the distance between the edge of the predetermined correction surface and the rotation-symmetrical edge is reduced according to a predetermined function, preferably linearly.

The spiral thus reduces in each revolution the distance between the edge of the predetermined correction surface and the rotation-symmetrical (circular) edge according to a predetermined function. In areas in which the distance between the non-rotation-symmetrical edge of the correction surface and the circular edge is a short distance, the paths thus become narrower, in areas in which there is a comparatively greater distance the paths are spaced further apart. The minimum or maximum distance between successive revolutions of the spiral can be set particularly easily through the number of rotations and the choice of the function.

If, as already mentioned, the transition area is formed as a flat surface the option suggests itself that the laser treatment device is adapted to focusing treatment laser radiation into the cornea along a main direction of incidence and to shift the position of the laser focus within the cornea, and the control data are generated such that they predetermine a path along which the laser focus is to be shifted, wherein the path lies in the predetermined correction surface and runs spirally from a center of the predetermined correction surface to an edge of the correction surface, wherein in a transition area the path is formed as spiral lying in the flat surface or as concentric circles, and for those sections of the spirals or concentric circles lying in the flat surface which would overlap with the correction surface when seen along the main direction of incidence, the control data provide a deactivation of the laser radiation with regard to its processing effect.

The processing laser beam is thus blanked, i.e. set such that there is no processing effect in those areas in which the spirals or the circles which form the flat surface would overlap with the correction surface. This can take place by controlling a suitable modulator or attenuator which sits in the beam path or by suitable control of the laser radiation source itself. Suitable means are known to a person skilled in the art, for example from US 2008/0021443 A1, the disclosure of which in this respect is included in its entirety.

The methods according to the invention of all variants for generating the control data can be carried out without recourse to human involvement. In particular they can be carried out by a computer which carries out the method according to the invention under the control of a program according to the invention and determines the control data for the laser from the corresponding presets. In particular when generating control data there is no need for the participation of a doctor as there is no therapeutic procedure involved in generating the control data. A therapeutic procedure takes place only when the previously determined control data are employed.

Where a method or individual steps of a method for generating control data for surgical correction of defective vision are described in this description, the method or individual steps of the method can be carried out using a correspondingly adapted device. This applies analogously to the explanation of the mode of operation of a device which carries out the method steps. To this extent the device and method features of this description are equivalent. In particular it is possible to realize the method with a computer on which a corresponding program according to the invention is executed.

Also, the features described here can be combined with one another as desired, as long as they do not technically contradict one another, in particular features of the first variant of the invention can be combined with features of the second variant.

BRIEF DESCRIPTION OF THE DRAWINGS

The invention is explained in even more detail below, by way of example, with reference to the drawings. There are shown in.

DETAILED DESCRIPTION

Figure 1:
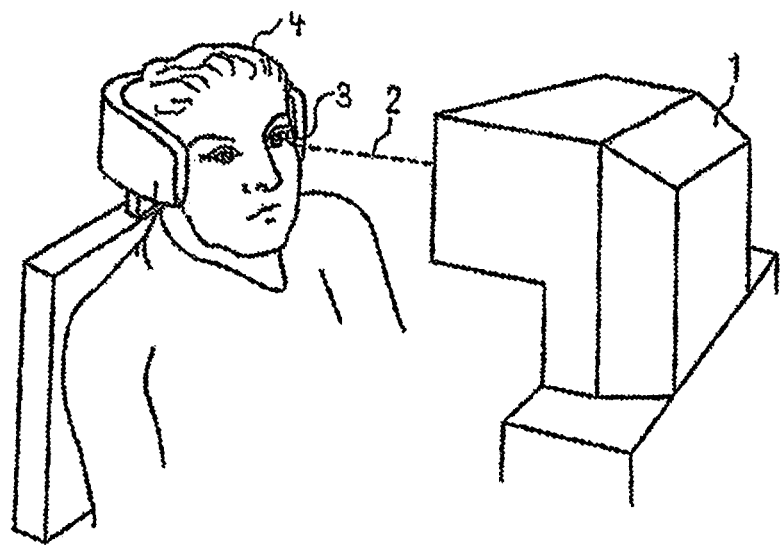
FIG. 1 a schematic representation of a treatment device or of a treatment apparatus for correcting defective vision, FIG. 2 a schematic representation of the structure of the treatment apparatus of FIG. 1, FIG. 3 a presentation showing the principle of introducing pulsed laser radiation into the eye when correcting defective vision with the treatment apparatus of FIG. 1, FIG. 4 a further schematic representation of the treatment apparatus of FIG. 1, FIG. 5 a schematic sectional representation through the cornea showing a volume to be removed for correcting defective vision, FIG. 6 a section through the cornea after removal of the volume of FIG. 5, FIG. 7 a sectional representation similar to that of FIG. 5, FIG. 8 a schematic sectional representation through the cornea to illustrate the volume removal, FIG. 9 a diagram with possible patterns of a distribution of optical refraction power which is used when determining the volume to be removed, FIG. 10 a flowchart for determining the volume to me removed, FIG. 11 a sectional representation through the cornea to illustrate an anterior and a posterior cut surface in combination with a top view of the posterior cut surface, wherein the designs of the cut surfaces correspond to the state of the art, FIG. 12 a sectional representation through the cornea to illustrate an anterior and a posterior cut surface in combination with a top view of the posterior cut surface, wherein a transition zone for adapting the cut surface to a circular edge is provided, FIG. 13 a representation similar to FIG. 12 for a differently shaped cut surface and a differently designed transition surface, FIG. 14 a representation similar to FIG. 13 for a cut surface effecting higher corrections, FIG. 15 a representation similar to FIG. 14, but for correcting defective vision with a flattening contact glass, FIG. 16 a representation similar to FIG. 15, but without transition zone, and FIG. 17 a representation similar to FIG. 16, but with a transition zone which matches a non-rotation-symmetrical edge.

FIG. 1 shows a treatment apparatus 1 for an eye-surgery procedure which is similar to that described in EP 1159986 A1 or in U.S. Pat. No. 5,549,632. By means of a treatment laser radiation 2 the treatment apparatus 1 effects a correction of defective vision on an eye 3 of a patient 4. Defective vision can include hyperopia, myopia, presbyopia, astigmatism, mixed astigmatism (astigmatism in which there is hyperopia in one direction and myopia in a direction lying at right angles thereto), aspherical errors and higher-order aberrations. In the embodiment described, the treatment laser radiation 2 is applied as a pulsed laser beam focused into the eye 3. The pulse duration in this case is e.g. in the femtosecond range, and the laser radiation 2 acts by means of non-linear optical effects in the cornea. The laser beam has short laser pulses of e.g. 50 to 800 fs (preferably 100-400 fs) with a pulse repetition frequency of between 10 and 500 kHz. In the embodiment described, the modules of the apparatus 1 are controlled by an integrated control unit, which, however, can of course also be formed as a stand-alone unit.

Before the treatment apparatus is used, the defective vision of the eye 3 is measured with one or more measuring devices.

Figure 2:
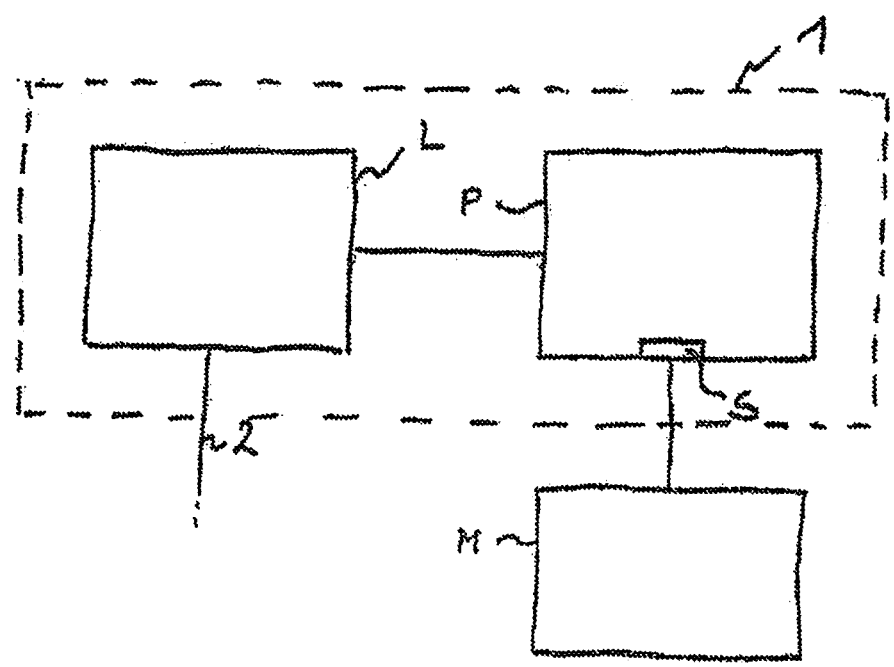
Figure 8:
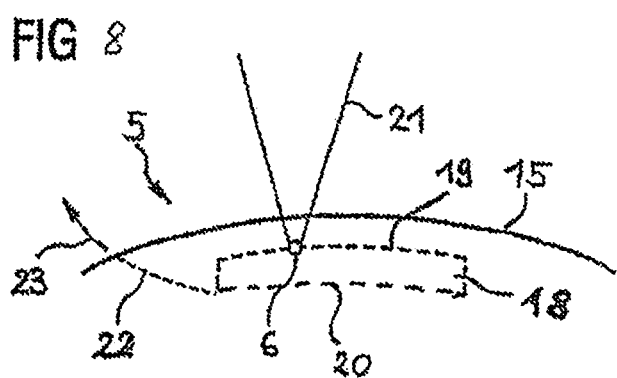

FIG. 2 shows the treatment apparatus 1 schematically. In this variant it has at least two devices or modules. A laser L emits the laser beam 2 onto the eye 3. The operation of the laser L in this case is fully automatic, i.e. in response to a corresponding start signal the laser L starts to deflect the laser beam 2 and thereby produces cut surfaces which, in a manner to be described, are built up and isolate a volume in the cornea. The laser L receives the control data necessary for operation beforehand from a planning device P as a control data set, via control lines that are not described in more detail. The data are transmitted prior to operation of the laser L. Naturally, communication can also take place wirelessly. As an alternative to direct communication, it is also possible to arrange the planning unit P physically separated from the laser L, and to provide a corresponding data transmission channel.

Preferably, the control data set is transmitted to the treatment apparatus 1 and more preferably, the operation of the laser L is blocked until there is a valid control data set at the laser L. A valid control data set can be a control data set which in principle is suitable for use with the laser L of the treatment device 1. Additionally, however, the validity can also be linked to the passing of further tests, for example whether details, additionally stored in the control data set, concerning the treatment apparatus 1, e.g. an appliance serial number, or concerning the patient, e.g. a patient identification number, correspond to other details that for example have been read out or input separately at the treatment device as soon as the patient is in the correct position for the operation of the laser L.

The planning unit P produces the control data set that is made available to the laser unit L for carrying out the operation from measurement data and defective-vision data which have been determined for the eye to be treated. They are supplied to the planning unit P via an interface S and, in the embodiment example represented, come from a measuring device M which has previously taken measurements of the eye of the patient 4. Naturally, the measuring device M can transfer the corresponding measurement and defective-vision data to the planning device P in any desired manner.

Transmission can be by means of memory chips (e.g. by USB or memory stick), magnetic storage (e.g. disks), by radio (e.g. WLAN, UMTS, Bluetooth) or wired connection (e.g. USB, Firewire, RS232, CAN-Bus, Ethernet etc.). The same naturally also applies with regard to the data transmission between planning device P and laser L.

A direct radio or wired connection of measurement device M to treatment device 1 with regard to data transfer which can be used in a variant has the advantage that the use of incorrect measurement and defective-eye data is excluded with the greatest possible certainty. This applies in particular if the patient is transferred from measuring device M or measuring devices to the laser L by means of a storage device (not represented in the Figure) which interacts with measuring device M or laser L such that the respective devices recognize whether the patient 4 is in the respective position for measurement or introduction of the laser radiation 2. By bringing the patient 4 from measuring device M to laser L the transmission of measurement and error-correction data to the treatment device 1 can also take place simultaneously.

Preferably it is ensured by suitable means that the planning device P always produces the control data set belonging to the patient 4 and an erroneous use of a false control data set for a patient 4 is as good as excluded.

Figure 3:
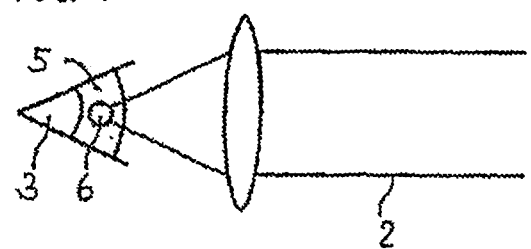

The mode of operation of the laser beam 2 is indicated schematically in FIG. 3. The treatment laser beam 2 is focused into the cornea 5 of the eye 6 by means of a lens which is not shown in more detail. As a result there forms in the cornea 5 a focus that covers a spot 6 and in which the energy density of the laser radiation is so high that, in combination with the pulse length, a non-linear effect in the eye results. For example, each pulse of the pulsed laser radiation 2 can produce at the respective spot 6 an optical break-through in the cornea 5 which, in turn, initiates a plasma bubble, indicated schematically in FIG. 3. As a result, tissue in the cornea 5 is cut disrupted this laser pulse. When a plasma bubble forms, the tissue layer disruption covers a larger region than the spot 6 covered by the focus of the laser radiation 2, although the conditions for producing the break-through are achieved only in the focus. In order for an optical break-through to be produced by every laser pulse, the energy density, i.e. the fluence, of the laser radiation must be above a certain threshold value which is dependent on pulse length. This relationship is known to a person skilled in the art from, for example, DE 69500997 T2.

Alternatively, a tissue-cutting effect can also be produced by the pulsed laser radiation by sending several laser radiation pulses into a region, wherein the spots 6 overlap for several laser radiation pulses. Several laser radiation pulses then act together to achieve a tissue-cutting effect.

The type of tissue cutting which the treatment apparatus 1 uses is, however, no further relevant for the description below, although pulsed treatment laser radiation 2 is described in this description. For example a treatment apparatus 1 such as is described in WO 2004/032810 A2 can be used. A large number of laser-pulse foci forms a cut surface in the tissue, the form of which depends on the pattern with which the laser-pulse foci are/become arranged in the tissue. The pattern specifies target points for the focus position at which one or more laser pulse(s) is (are) emitted and defines the form and position of the cut surface.

In order now to carry out a correction of defective vision, material is removed from a region within the cornea 5 by means of the pulsed laser radiation by cutting tissue layers thus isolating the material and then make it possible for material to be removed. The removal of material effects a change in the volume of the cornea which results in a change in the optical imaging effect of the cornea 5, which change is calculated exactly such that the previously determined defective vision thus is/becomes corrected as much as possible. To isolate the volume to be removed, the focus of the laser radiation 2 is directed towards target points in the cornea 5, generally in an area which is located beneath the epithelium and the Bowman's membrane and above the Decemet's membrane and the endothelium. For this purpose the treatment apparatus 1 has a mechanism for shifting the position of the focus of the laser radiation 2 in the cornea 5. This is shown schematically in FIG. 3.

In FIG. 4, elements of the treatment apparatus 1 are shown only as long as they are necessary to understand the shifting of the focus. As already mentioned, the laser radiation 2 is bundled in a focus 7 in the cornea 5, and the position of the focus 7 in the cornea is shifted such that, to produce cut surfaces, energy from laser radiation pulses is introduced into the tissue of the cornea 3 focused at various points. The laser radiation 2 is provided by a laser 8 as pulsed radiation. An xy scanner 9 which, in one variant, is realized by two substantially orthogonally deflecting galvanometric mirrors, deflects the laser beam of the laser 8 in two dimensions such that there is a deflected laser beam 10 after the xy scanner 9. The xy scanner 9 thus effects a shifting of the focus 7 substantially perpendicular to the main direction of incidence of the laser radiation 2 into the cornea 5. To adjust the depth position a z scanner 11 which is realized, for example, as an adjustable telescope, is provided in addition to the xy scanner 9. The z scanner 11 ensures that the z position of the focus 7, i.e. its position on the optical incidence axis, is changed. The z scanner 11 can be arranged before or after the xy scanner 9. The coordinates designated x, y, z in the following thus relate to the deflection of the position of the focus 7.

The allocation of the individual coordinates to the spatial directions is not essential for the operating principle of the treatment apparatus 1; but to simplify the description, in the following the coordinate along the optical axis of incidence of the laser radiation 2 is always designated z, and x and y designate two coordinates orthogonal to one another in a plane perpendicular to the direction of incidence of the laser beam. It is naturally known to a person skilled in the art that the position of the focus 7 in the cornea 5 can also be described three-dimensionally by other coordinate systems, in particular that the coordinate system need not be a rectangular system of coordinates. Thus it is not essential for the xy scanner 9 to deflect around axes that are at right angles to one another; rather, any scanner capable of shifting the focus 7 in a plane in which the incidence axis of the optical radiation does not lie can be used. Oblique-angled coordinate systems are thus also possible.

Further, non-Cartesian coordinate systems can also be used to describe, or control, the position of the focus 7, as will also be explained further below. Examples of such coordinate systems are spherical coordinates as well as cylindrical coordinates.

To control the position of the focus 7, the xy scanner 9 as well as the z scanner 11, which together realize a specific example of a three-dimensional focus-shifting device, are controlled by a control apparatus 12 via lines not described in more detail. The same applies to the laser 8. The control apparatus 3 ensures a suitably synchronous operation of the laser 8 as well as the three-dimensional focus-shifting device, realized by way of example by the xy scanner 9 and the z scanner 11, with the result that the position of the focus 7 is shifted in the cornea 5 such that, ultimately, a specific volume of material is isolated, wherein the subsequent volume removal effects a desired correction of defective vision.

The control apparatus 12 operates according to predetermined control data which predetermine the target points for shifting the focus. The control data are generally collected in a control data set. In one embodiment, this predetermines the coordinates of the target points as a pattern, wherein the sequence of the target points in the control data set fixes the serial arrangement of the focus positions alongside one another and thus, ultimately, a path curve (also referred to here in short as a path). In one embodiment, the control data set contains the target points as specific reference values for the focus-shifting mechanism, e.g. for the xy scanner 9 and the z scanner 11. To prepare the eye-surgery procedure, thus before the actual operation can be carried out, the target points and preferably also their order are determined in the pattern. There must be pre-planning of the surgical procedure to determine the control data for the treatment apparatus 1, the application of which then achieves an optimal correction of defective vision for the patient 4.

Firstly, the volume to be isolated in the cornea 5 and later removed must be defined. As already described with reference to FIG. 2 this requires to establish the need for correction.

With regard to the nomenclature used in this description it may be noted that the addition of an asterisk to values indicates that these are values which are obtained after a correction. On the justified assumption that a change in thickness of the cornea 5 substantially modifies the radius of curvature of the front face 15 of the cornea facing the air, but not the radius of curvature of the rear 16 of the cornea adjacent to the inside of the eye, the radius of curvature $R_{CV}$ of the front of the cornea 15 is modified by the volume removal. Because of the modified curvature of the front having changed cornea surface 15*, the cornea 5 reduced by the volume has a correspondingly modified imaging effect, with the result that there is now a corrected focus on the retina 14.

To determine the pattern of the target points, the curvature to be achieved $R_{CV}^*$ of the cornea front surface 15* is therefore determined.

Using the value $B_{COR}$, the curvature of the modified cornea front surface 15* is now set as follows:

$$R_{CV}^*(r,\varphi)=1/((1/R_{CV}(r,\varphi))+B_{COR}(r,\varphi)/(n_c-1))+F, \quad (1)$$

In equation (1) $n_c$ denotes the optical refraction power of the material of the cornea. The proper value is usually 1.376; $B_{COR}$ denotes a change in optical refraction power which is necessary to correct defective vision. $B_{COR}$ is radially dependent. By radial dependence is meant that there are two values r1 and r2 for the radius r for which the change in optical refraction power has different values at all angles $\varphi$.

Figure 9:
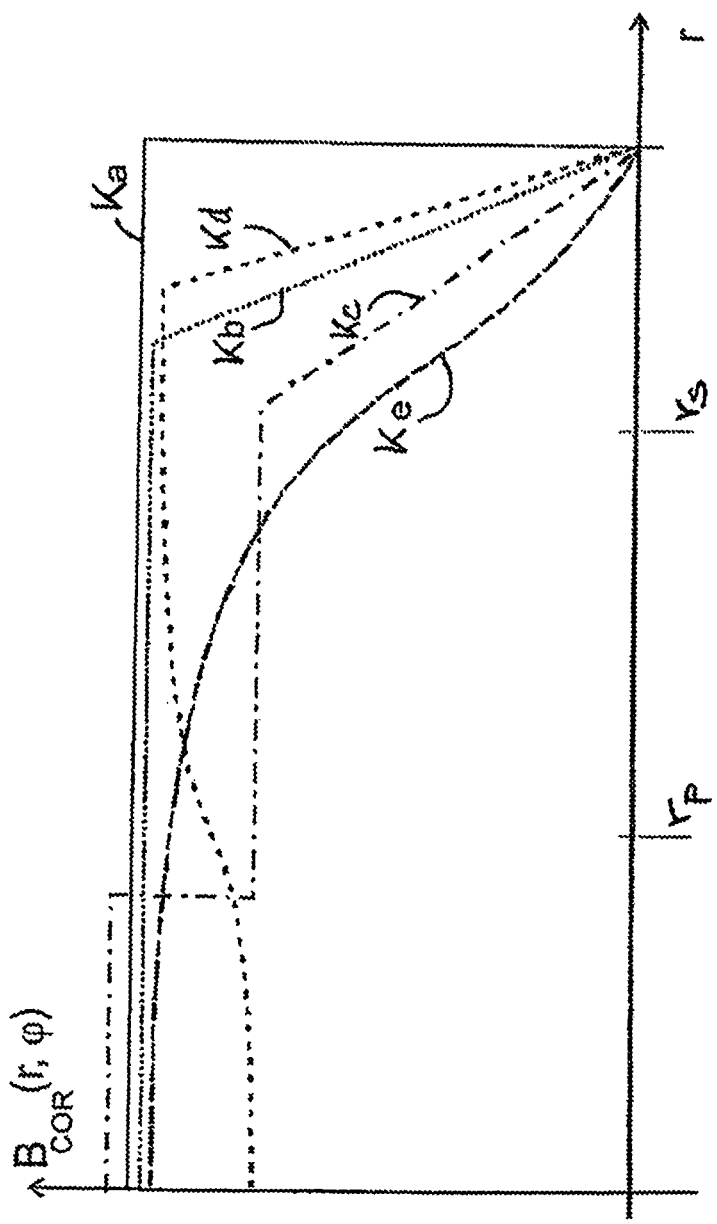

Examples of possible patterns of changes in optical refraction power are shown by way of example in FIG. 9 which shows the function $B_{COR}$ in different exemplary curves Ka to Ke as a function of the radius r.

Ka is the conventional refractive index of spectacles from the state of the art according to DE 102006053120 A1, but already referenced to the plane of the vertex of the cornea in the representation of FIG. 9. In the cited state of the art there is no reason for such reference relationship. It has been included here only for the purpose of better comparability with the exemplary curves Kb to Ke according to the invention. The curve Kb is constant up to a radius which lies beyond a radius $r_s$, and then falls. The radius $r_s$ is thus the scotopic pupil radius, i.e. the pupil radius at night vision. The change in optical refraction power according to curve Kc is partly constant as far as radius $r_s$, wherein below a radius $r_p$, which corresponds to the photopic pupil radius, there is a sudden drop from a higher value to a lower value. Such a variation of the correction in optical refraction power over the cross-section of the pupil is particularly advantageous in the case of farsightedness in old age. Near vision usually occurs under good lighting, e.g. when reading. The pupil is then generally contracted to the photopic pupil radius because of the good lighting. The correction in optical refraction power then necessary sets an optimum adaptation to near vision, e.g. an optimum viewing distance of approximately 25 to 70 cm. For the other extreme case, namely night vision, which is usually linked with looking into the distance (e.g. when driving at night), on the other hand, the pupil is opened to its maximum. Then, areas of the pupil which have a different (e.g. lower) value for correcting optical refraction power also contribute to optical imaging. The human brain is capable of correcting imaging having such visual errors (different position of focus for the centre of the pupil and edge areas of the pupil) in visual perception. The correction of optical refraction power curves shown in the curves Kc or Kd thus allow, consciously accepting an imaging error, the enlargement of the focus depth range, as the imaging error is compensated for by the brain.

The correction of optical refraction power then drops again from pupil radius $r_s$. The unstepped drop in the correction of optical refraction power to zero is advantageous from an anatomical point of view. It allows, at the edge of the corrected range, i.e. at the edge of the volume to be removed, an adaptation of the corrected cornea front radius which is set, on the basis of the correction, to the original radius of curvature of the cornea, i.e. the pre-operative radius. Reverting to the representation of FIG. 5 this means that there is an adjustment of these radii in the edge area of the volume to be removed at which the radii $R_F$ and $R_L$ converge in the representation of FIG. 5. As a result, the transition from the new cornea front-side radius $R^*_{CV}$ which occurs in the area in which the volume 18 has been removed to the original radius of curvature of the cornea $R_{CV}$ is comparably soft. The optical correction is thus overall better, which can be achieved only because of the radially varying the correction of optical refraction power.

The drop in the correction of optical refraction power to zero takes place preferably in an area outside the darkened pupil radius, thus in an area of the cornea no longer relevant for vision.

The curve Kd shows a similar pattern, but here there is a smooth transition from the first value of the change in optical refraction power below $r_p$ to the second value at $r_s$. Also, by way of example, the first value here is lower than the second value. This can naturally also be used for the curve Kc, depending on the desired requirement for correction. Curve Ke shows a continuous decline.

The locally varying changes in optical refraction power, described with reference to FIG. 9, with radial dependence, are examples of a change in optical refraction power which is used when determining the volume to be removed in the operation.

The coefficient F expresses the optical effect of the change in thickness which the cornea experiences as a result of the surgical procedure and can be seen in a first approximation as a constant coefficient which can be determined e.g. experimentally in advance. For a highly accurate correction the coefficient can be calculated according to the following equation:

$$F=(1-1/n_c)\cdot \Delta z(r=0,\varphi) \qquad (2)$$

$\Delta z(r=0, \varphi)$ is the central thickness of the volume to be removed.

For a precise determination, $R_{CV}^*$ is iteratively calculated by determining in an nth calculation step the value $\Delta z(r=0,\varphi)$ from the difference $1/R_{CV}^*(r=0,\varphi)-1/R_{CV}\Delta r=0,\varphi)$ and using the corresponding result obtained from this for the change in thickness in the (n+1)th calculation step as new value for $R^*_{CV}$. This can be carried out until an abort criterion is met, for example if the difference in the result for the change in thickness in two successive iterations lies below a suitably fixed limit. This limit can for example be set as a constant difference which corresponds to an accuracy of the refraction correction that is appropriate to the treatment.

Figure 10:
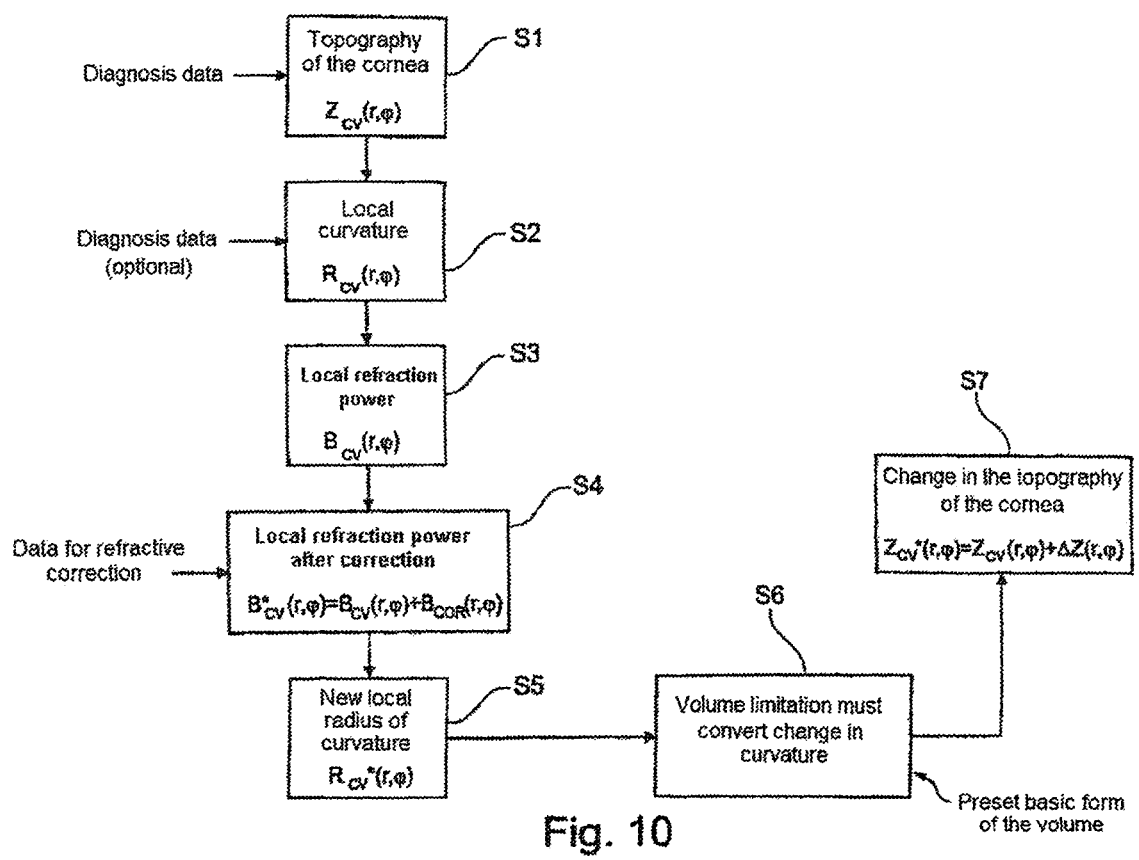
Figure 11:
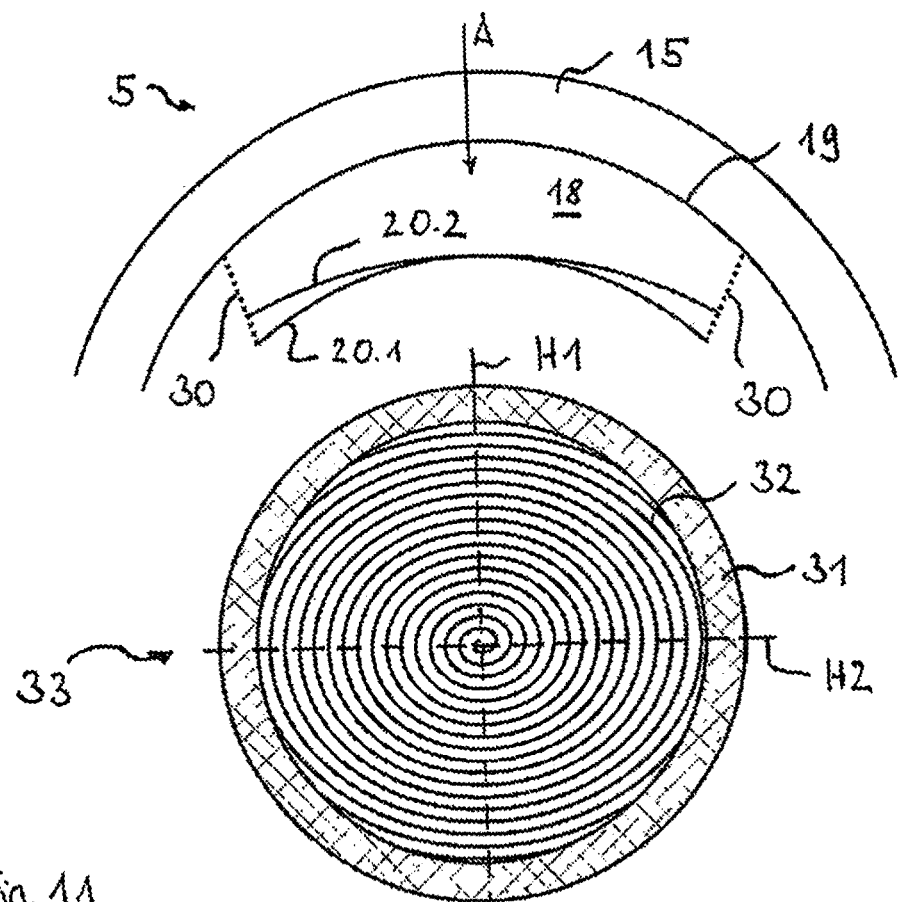

In general the method represented in FIG. 10 can be carried out. In a step S1 the topography of the cornea is calculated from diagnosis data, as mentioned already at the start in the general section of the description. The radial curvature of the front 15 of the cornea is determined from this topography. This can also be directly determined from the diagnosis data, instead of the topography data from step S1, with the result that step S2 is either placed after step S1 or diagnosis data are directly evaluated as FIG. 10, shows by adding "(optional)". Thus step S1 is optional.

The local optical refraction power of the cornea is determined in a step S3.

The required local change in optical refraction power $B_{COR}$ is determined from data relating to the desired refractive correction in a step S4 and the local optical refraction power desired after the correction determined from this local change in optical refraction power.

The new local radius of curvature $R^*_{CV}(r,\varphi)$ is generated then in step S5. Instead of the calculation of the local optical refraction power $B_{CV}$ in step S3, calculation can also take place directly with the local curvature $R_{CV}$ from step S2 if the above equation (1) is used. It should be pointed out quite basically that optical refraction power and radius of curvature can be transformed into each other by a simple equation. Thus: $B=(n_C-1)/R$, wherein B is the optical refraction power and R the radius allocated to this optical refraction power. Thus, within the framework of the invention, it is possible at any time to alternate between radius approach and optical refraction power approach or representation. The equation to be used when determining control data in optical refraction power representations is:

$$B^*_{CV}(r,\varphi) = \cfrac{1}{\cfrac{1}{B_{CV}(r,\varphi)+B_{COR}(r,\varphi)}+\cfrac{F}{(n_C-1)}}$$

When the radius of the cornea surface is mentioned here, the optical refraction power can also be used completely analogously, with the result that all statements made here in connection with the radius of the cornea surface self-evidently also apply analogously to the representation or consideration of the optical refraction power if R is replaced by B according to the named dependency.

For the volume whose removal effects the above change in curvature of the cornea front surface 15 the boundary surface isolating the volume is now defined in a step S6. Account is to be taken of what basic form the volume is to have.

In a first variant by numerical methods known to a person skilled in the art a free from surface is defined which circumscribes the volume whose removal effects the change in curvature. The volume thickness required for the desired modification in curvature is determined along the z axis. This gives the volume a function of r, φ (in cylinder coordinates) and the boundary surface is defined based on the volume.

Figures 5, 6:
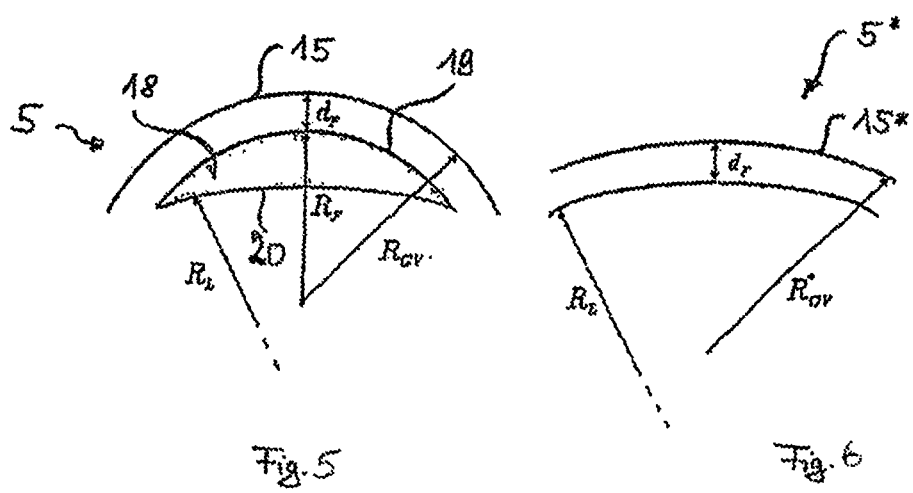

On the other hand an analytical calculation is delivered by the following variant, already discussed in DE 102006053120 A1, in which the boundary surface of the volume is essentially built up from two surface parts, an anterior surface part facing the cornea surface 15 and an opposite posterior surface part. FIG. 5 shows the corresponding relationships. The volume 18 is limited towards the cornea front 15 by an anterior cut surface 19 which is at a constant distance $d_F$ below the cornea front surface 15. This anterior cut surface 19 is also called flap surface 19 by analogy with the laser keratomes as it serves, in combination with an opening section towards the edge, to be able to raise a flap-shaped lamella from the cornea 5 from the cornea 5 beneath. This way of removing the previously isolated volume 18 is naturally possible here also.

The anterior cut surface 19 is preferably spherical as then a radius of curvature which is smaller by the thickness of a lamella $d_F$ than the radius of curvature $R_{CV}$ can be defined.

To the rear the volume 18 which is to be removed from the cornea 5 is limited by a posterior cut surface 20 which already basically cannot be at a constant distance from the cornea front surface 15. The posterior cut surface 20 is therefore formed such that the volume 18 has the form of a lenticle, which is why the posterior cut surface 20 is also called lenticle surface. This surface is shown in FIG. 5 by way of example as a likewise spherical surface with a radius of curvature $R_L$, wherein in FIG. 5 naturally the center of this curvature does not coincide with the center of curvature of the likewise spherical cornea front surface 15. The two surfaces 19, 20 are preferably connected at their edge by a lenticle edge surface in order to completely circumscribe the volume to be removed and simultaneously guarantee a minimum thickness at the edge.

FIG. 6 shows the situation after the volume 18 has been removed. The radius of the modified cornea front surface 15* is now $R_{CV}^*$ and can for example be calculated according to the previously described equations. The thickness $d_L=\Delta z(r=0,\varphi)$ of the removed volume 18 governs the change in radius, as illustrated by FIG. 7. The lenticle surface is simplified to be spherical in this figure. Consequently, the height $h_F$ of the ball cap defined by the flap surface 19, the height $h_L$ of the ball cap defined by the lenticle surface 20 and the thickness dL of the volume 18 to be removed are shown.

Due to the constant distance between cornea front surface 15 and flap surface 19, the lenticle surface 20 defines the curvature of the cornea front surface 15* after the volume 18 has been removed.

If the coefficient F is to be taken into account during calculation, in step S7 the change in topography of the cornea are considered, too, i.e. the current central thickness is computed. Using the resulting value for the coefficient F, steps S4 to S6 or S5 to S6 can then be carried out once again or repeatedly in the form of an iteration.

The formation shown in the figures of the volume 18, as limited by a flap surface 19 at a constant distance from the cornea front surface 15 and a lenticle surface 20, is only one variant for limiting the volume 18. However, it has the advantage that the optical correction is given essentially by only one surface (the lenticle surface 20), with the result that the analytical description of the other surface part of the boundary surface is simple.

Furthermore, safety margins with regard to the distance between the volume and cornea front surface 15 and cornea back surface 16 are optimal. The residual thickness $d_F$ between flap surface 19 and cornea front surface 15 can be set to a constant value, e.g. 50 to 200 µm. In particular it can be chosen such that the pain-sensitive epithelium remains in the lamella which is formed by the flap surface 19 beneath the cornea front surface 15. The formation of the spherical flap surface 19 is also continuous with previous keratometer sections which is advantageous in terms of acceptance of the method.

After producing the cut surfaces 19 and 20 the thus-isolated volume 18 is then removed from the cornea 5. This is represented schematically in FIG. 9 which also shows that the cut surfaces 19 and 20 are produced by the action of the incident treatment laser beam by exposure to a focus sphere 21, for example by the arrangement of plasma bubbles alongside one another, with the result that in a preferred embodiment the flap surface 19 and the lenticle surface 20 are produced by suitable three-dimensional shifting of the focus position of the pulsed laser radiation 2.

Alternatively in a simplified embodiment, however, merely the flap surface 19 can also be formed, by means of pulsed laser radiation, by target points which define the curved cut surface 19 at a constant distance from the cornea front surface 15, and the volume 18 is removed by laser ablation, for example by using an excimer laser beam. For this, the lenticle surface 20 can be defined as boundary surface of the area removed, although this is not essential. The treatment apparatus 1 then operates like a known laser keratome, but the cut surface 19 is produced using curved cornea. The previously or subsequently described features are also possible in such variants, in particular as regards the determination of the boundary surface, its geometric definition and determining control parameters.

If both the lenticle surface 20 and the flap surface 19 are produced by means of pulsed laser radiation it is expedient to form the lenticle surface 20 prior to the flap surface 19, as the optical result is better with the lenticle surface 20 (if not achievably only then) if there has still been no change in the cornea 5 above the lenticle surface 20.

Figure 12:
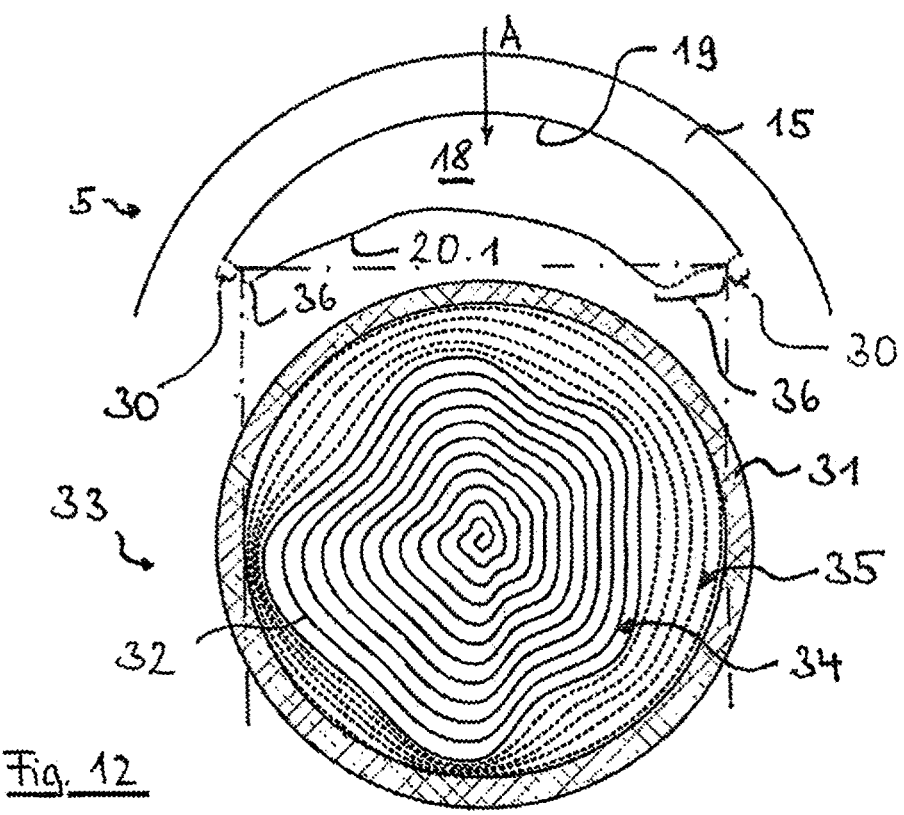

FIG. 12 shows a representation, the upper part of which corresponds basically to the view of FIG. 5. In the lower part, a top view 33 of the lenticle surface 20 is shown which is illustrated in the sectional representation lying above it by only a section line 20.1.

To isolate the volume 18, firstly the flap surface 19 and also the lenticle surface 20 is produced in the cornea 5 in the manner described. A correction surface is produced which is non-rotation-symmetrical in order to correct higher aberrations, thus the curvature of the front side 15 of the cornea 5 is to be changed after removal of the volume 18 not just with regard to sphericity. As the top view 33 on the lenticle surface 20 shows, this correction surface is produced by a spiral 32 which runs outwards from the inside of the correction surface. The spiral defines a path curve for shifting the position of the laser-beam focus. The centre of the spiral preferably (but not necessarily) lies at the highest point of the correction surface. The spiral is based on contour lines, whereby the z position (position along the main direction of incidence A of the laser radiation) of the focus position is continuously shifted. Instead of a group of closed scan lines which never intersect there is a continuous scan line. Local varying corrections of an optical refraction power $B(r, \varphi)$ can be easily represented and obtained by modulation of an angle-dependent radial function $r(\varphi)$ by a thus radially "deformed" spiral.

The edge line of the lenticle surface 20 is to be a circular line which lies in z direction which, as usual, is the main direction of incidence A of the treatment laser radiation. Thus z=const for the edge $r_{MAX'}(f_P, \varphi)$ of the lenticle surface 20. The correction surface which is required for optical correction is defined in a correction area 34. Here, the path curve is shown continuous. The edge of this correction area is naturally not rotation-symmetrical—but is level, as the spiral is based on contour lines. Therefore there is a modification of the spiral in a transition area 35 such that, within a limited number of revolutions, the angle-dependent distance relative to the path is modulated such that the non-rotation-symmetrical edge of the correction surface changes to a circle. The radial modulation is thus reduced to zero over a specific number of revolutions. For example this can take place by choosing the number of revolutions of the spiral in the transition area such that it corresponds to the quotient from the difference in radii and the desired distance between the spiral paths. The difference in radii is the difference between the minimum radius of the correction surface and the radius of the desired circular edge which is preferably equal to, or only slightly larger than, the maximum radius of the correction surface.

This continuation of the spiral in the transition area 34 continues the correction surface, which is the cut surface geometry in the correction area 34, such that it terminates in a circular edge. This can be clearly seen in the relationships of the sectional representations in which dot-dashed reference lines are drawn-in for illustration. Furthermore, the continuation of the correction surface in the transition area is represented in the sectional representation by the same dotted line as the corresponding spiral revolutions in the top view 33 of the lenticle surface 20. The sectional representation shows that the rim of the lenticle surface 20 lies in a plane. Furthermore, it is circular. Therefore, the connection between the lenticle surface 20 and the spherical flap surface 19 can be produced by a simple lenticle edge surface 30 in the shape of a circle cone envelope.

There are no sections of the lenticle edge surface 30 or of the flap surface 19 which would be introduced into the cornea and which are not required for connection to the lenticle surface 20.

It is essential, to understand the embodiments described here, to distinguish between the transition area 35 and the lenticle-edge area 31 (corresponding to the cut surfaces 36 and 30). The transition zone thus adapts the otherwise non-rotation-symmetrical correction surface such that the lenticle surface 20 as a whole has a rotation-symmetrical edge. This edge is not lower, i.e. more posterior, than that of the correction surface (corresponding to the cutting line) but also not higher, i.e. more anterior. The plane in which the circular edge is formed by the transition area 35 thus cuts the correction surface or lies at least on the maximum or minimum of this surface. The correction surface is thus complemented by the transition zone, but is to be distinguished from the lenticle edge surface which, as simple circular cylindrical or cone-envelope-shaped cut surface produces the connection between two rotation-symmetrical edges, namely that of the lenticle surface 20 which has been reached through the transition zone 35, and that of the flap surface 19 (already spherical, in any case, in the described embodiment).

Figure 14:
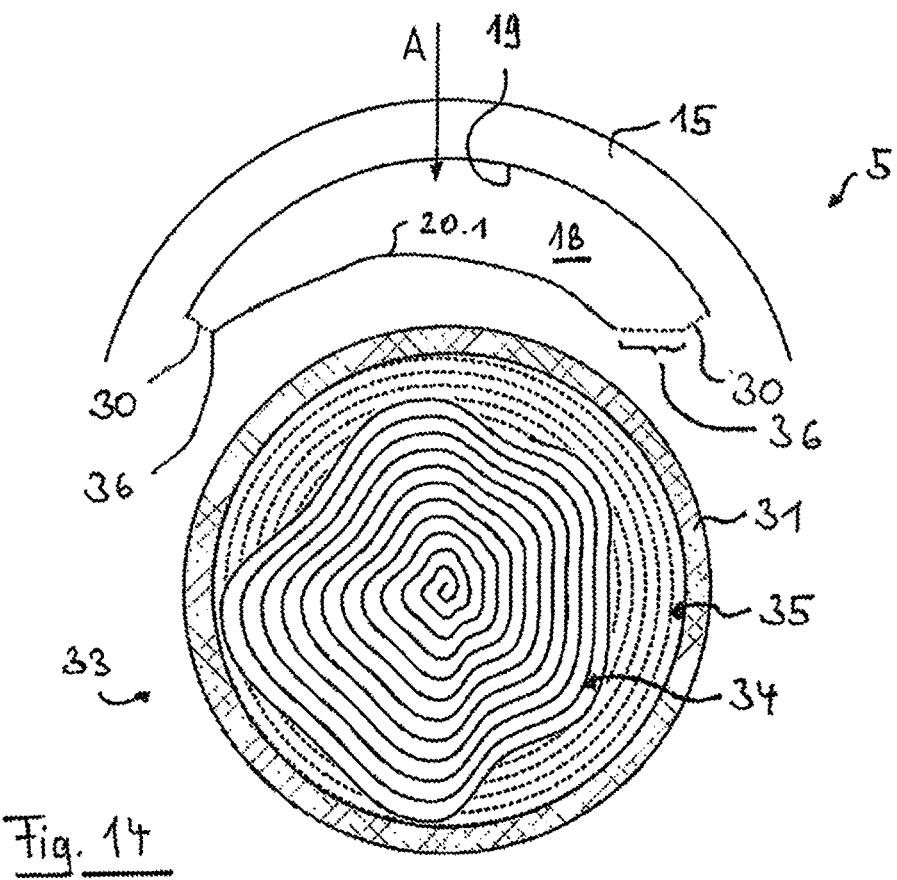

FIG. 12 shows an embodiment in which the transition zone 35 forms a continuous and flat, e.g. differentiable, adaptation between the edge surface of the correction surface (cut surface in the correction zone 34) and the circular edge. Such a flat course is not, however, essential, as FIG. 14 shows.

Figure 13:
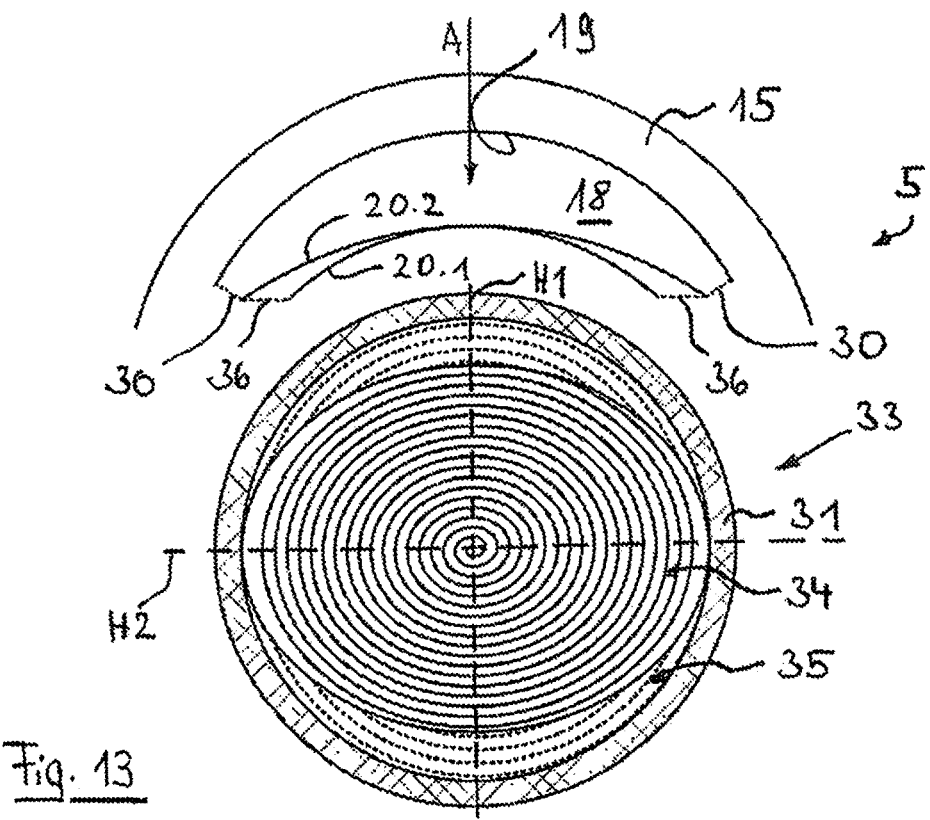

In FIG. 13 the correction zone 34 is predetermined in this case by the correction surface which, by way of example, is formed as an ellipsoid for correcting astigmatism. The sectional representation of the lenticle surface 20 therefore shows two cuts 20.1 and 20.2, which correspond to the semiaxes H1 and H2 of the ellipsoid surface in the correction zone 34. Another way is also chosen to complete the correction zone 34 by the transition zone 35 such that overall there is a rotation-symmetrical, i.e. circular edge. Again, the lenticle surface 20 is produced by a spiral-shaped path along which the focus of the laser radiation is shifted, as can be seen from the top view 33. If the edge of the correction zone 34 is reached, as already mentioned in the general section of the description, which is defined either by the edge of the predetermined correction surface or results from the production of a larger correction surface over the desired pupil cross-section, the spiral curve pattern of the path is converted into a circular spiral with a constant z value.

Thus there is in the transition zone 35 a spiral with a constant distance relative to the path which is guided from the smallest radius of the correction surface in the correction zone 34 as far as the radius of the rotation-symmetrical edge which, expediently, is equated with the largest radius of the edge of the correction zone 34. However, the transition zone can optionally be overmeasured to a certain degree, thus the chosen radius of the rotation-symmetrical edge can be larger by an overmeasure than the largest radius of the correction surface in the correction zone 34.

When shifting along this spiral with a constant path distance, however, a laser treatment is suppressed at those path sections whose positions would lie within the correction zone or within the periphery of the correction zone 34. In the case of laser treatment by pulsed laser radiation for example according to the concept of DE 10358927 A1 the disclosure of which in this regard is incorporated in its entirety, the laser radiation pulse is made "harmless" with regard to its processing effect. It is shown in the sectional representation of FIG. 13 that through the spiral with constant path distance and fixed z value the transition zone 34 results in a continuation of the posterior cut surface which is depicted as transition cut surface 36 and lies perpendicular to the direction of incidence A of the laser radiation. The extent of this transition cut surface 36 depends naturally on the distance between the edge of the non-rotation-symmetrical correction surface or correction zone 34 and the rotation-symmetrical edge. This results in the transition cut surface 36 of FIG. 14 in the sectional representation being very much longer on the right-hand side than on the left-hand side, where it is virtually punctiform as the rotation-symmetrical edge was chosen to be almost equal to the maximum radius of the correction zone 34.

The representation in FIG. 14 corresponds essentially to that of FIG. 13. However, the correction surface or the correction zone 34 is not ellipsoidal here, thus not elliptical in the top view 33, but adapted to the correction of higher aberrations. Otherwise, what was said above with regard to FIG. 13 applies also without limitation to FIG. 14, which shows that the design of the transition zone of FIG. 13 need not necessarily be associated with an ellipsoidal correction surface.

FIG. 15 shows an embodiment in which the cornea 5 is flattened by means of a flat contact glass. The flap surface 19 is therefore formed as a plane. Also, the lenticle edge zone 31 appears in the top view 33 as just a line. The transition zone 35 is formed analogously to the embodiment of FIGS. 13 and 14 as a flat spiral with a constant path radius. What was said with regard to FIGS. 13 and 14 thus applies to the same extent.

The transition zone 35 is thus a planar spiral with a constant distance relative to the path which runs from the small semiaxis H1 as far as the large semiaxis H2 of the elliptical correction zone 34 to reach the circular edge.

In the embodiment of FIG. 15 the lenticle edge surface is designed as a circular cylinder in which it is ensured that the edge radius of the flap surface 19 is equal to the edge radius of the lenticle surface 20 and that, furthermore, the edges lie precisely beneath one another. However, this is not essential. Different radii can be used and the circular edges offset relative to one another. Circular inclined cylinders or oblique circular cylinder surfaces are then required for the lenticle surface.

FIG. 16 shows an embodiment which does not form part of the invention of the first variant, in which no transition zone 35 is provided. Instead there a non-rotation-symmetrical lenticle edge surface 30 is formed direct connecting flap surface 19 to the non-rotation-symmetrical edge of the correction zone 34. This surface is a cylinder surface, the generatrix of which corresponds to the edge of the correction zone 34.

Figure 17:
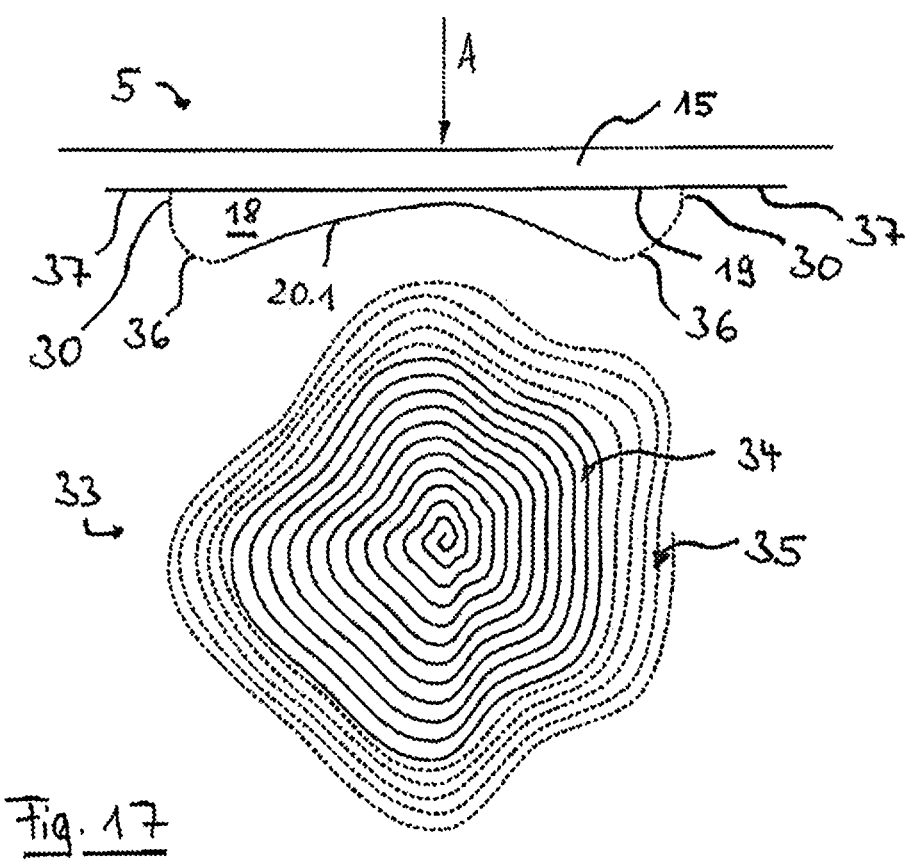

Equally, the invention of the first variant does not realize the embodiment of FIG. 17 in which a transition zone 35 is provided which continues the correction zone 34 by reducing the z coordinate such that the transition zone 35 is directly extended to the flap surface 19, maintaining the non-rotation-symmetrical circumference. The transition zone is thus produced such that, within a limited number of revolutions, the angle-dependent path distance is modulated such that the edge of the correction zone 34 is brought to the flap surface 19 with regard to the z coordinate.

The use of pulsed laser radiation is not the only way in which surgical refraction correction can be carried out. The determination, described here, of control data for operating the device can be used for almost any operating procedure in which, by means of a device, with control by control data, a volume is removed from the cornea or added to it, as already explained in the general section of the description.

The invention claimed is:

1. A control data generating device for generating control data that control a laser system for surgical correction of defective vision of an eye of a patient by emitting laser radiation to generate at least one cut in a cornea of the eye, the control data generating device comprising:

a computer operating under control of a program, the computer and the program together being configured to generate the control data to control the laser system to focus the laser radiation to different focus positions located within the cornea such that the at least one cut isolates a subsurface volume in the cornea, the subsequent removal of which subsurface volume from the cornea effects a desired correction of the defective vision, the computer being operatively coupled to the laser system, wherein the laser system includes at least a laser and optics for emitting laser radiation to generate the at least one cut in the cornea of the eye, the computer and the program together being configured to determine the control data by calculating an optical parameter of the cornea reduced by the subsurface volume, wherein the optical parameter is locally varying and the optical parameter is either a radius of curvature $R^*_{CV}(r,\varphi)$ of the cornea reduced by the subsurface volume or an optical refraction power $B^*_{CV}(r,\varphi)$ the cornea has without the subsurface volume, wherein the optical parameter is the optical refraction power $B^*_{CV}(r,\varphi)$ the cornea has without the subsurface volume and wherein the computer and the program together are configured to calculate optical refraction power $B^*_{CV}(r,\varphi)$ using the following equation:

$$B^*_{CV}(r,\varphi) = \frac{1}{\frac{1}{B_{CV}(r,\varphi)+B_{COR}(r,\varphi)}+\frac{F}{(n_C-1)}}$$

wherein $B_{CV}(r,\varphi)$ is a local optical refraction power of the cornea before the subsurface volume is removed, $n_c$ is the refractive index of the material of the cornea, F is a coefficient, and $B_{COR}(r,\varphi)$ is a local change in optical refraction power in a plane lying in the vertex of the cornea and required for the desired correction of the defective vision, and the computer and the program together being configured to transfer the control data to the laser system to guide the laser system during a surgical procedure, the laser system using the control data to direct laser radiation to generate the at least one cut in the cornea of the eye.

2. The control data generating device according to claim 1, wherein when determining the control data, the computer and the program together are configured to define the optical parameter to be angle-independent.

3. The control data generating device according to claim 1, wherein the computer and the program together are configured to generate the control data to prescribe a path of focus positions for the laser radiation within the cornea wherein the path is located in the least one cut within the cornea and wherein the focus is to be shifted over the path to generate the at least one cut within the cornea.

4. The control data generating device according to claim 1, wherein the optical parameter further comprises the radius of curvature $R^*_{CV}$ of the cornea reduced by the volume radius of curvature and wherein the radius of curvature $R^*_{CV}$ satisfies the following equation:

$R^*_{CV}(r,\varphi)=1/((1/R_{CV}(r,\varphi))+B_{COR}(r,\varphi)/(n_c-1))+F,$ wherein $R_{CV}(r,\varphi)$ is a local radius of curvature of the cornea before the subsurface volume is removed, $n_c$ is the refractive index of the material of the cornea, F is a coefficient, and $B_{COR}(r,\varphi)$ is a local change in optical refraction power in a plane lying in the vertex of the cornea and required for the desired correction of the defective vision.

5. The control data generating device according to claim 4, wherein the computer and the program together are configured to use $F=(1-1/n_c)\cdot\Delta z(r=0,\varphi)$ for the coefficient F, wherein $\Delta z(r=0,\varphi)$ is the central thickness of the subsurface volume to be isolated in the cornea and removed, and wherein the computer and the program together are configured to iteratively calculate the radius of curvature $R^*_{CV}(r,\varphi)$, wherein the computer and the program together are configured to derive in each iteration step the central thickness $\Delta z(r=0, \varphi)$ of the subsurface volume from the difference between the central reciprocal radii of curvature $1/R^*_{CV}(r=0,\varphi)$ and $1/R_{CV}(r=0,\varphi)$, and applies this value when calculating $R^*_{CV}(r,\varphi)$ in a next iteration step.

6. The control data generating device according to claim 1, wherein, when determining the control data, the control data generating device defines at least two radii, r1 and r2, for which $B_{COR}(r=r1,\varphi)\neq B_{COR}(r=r2,\varphi)$ holds true, wherein $B_{COR}(r,\varphi)$ is a local change in optical refraction power in a plane lying in the vertex of the cornea and required for the desired correction of the defective vision.

7. The control data generating device according to claim 1, wherein, when determining the control data, the control data generating device defines the local change in optical refraction power $B_{COR}(r,\varphi)$ such that there is a characteristic radius Ich for which a radial function of the change in optical refraction power $B_{COR}(r,\varphi)$ is piecewise constant, for which radii thus $B_{COR}(r<r_{ch}, \varphi=const)=B_a\neq B_b=B_{COR}(r>r_{ch}, \varphi=const)$ holds true, wherein $B_{COR}(r,\varphi)$ is a local change in optical refraction power in a plane lying in the vertex of the cornea and required for the desired correction of the defective vision.

8. The control data generating device according to claim 1, wherein, when determining the control data, the control data generating device defines the local change in optical refraction power $B_{COR}(r,\varphi)$ such that there are two radii $r_a$ and $r_b$ for which a radial function of change in optical refraction power $B_{COR}(r,\varphi)$ is piecewise constant, for which radii thus $B_{COR}(r<r_a,\varphi=const)=B_a\neq B_b=B_{COR}(r>r_b,\varphi=const)$ holds true, wherein the radial function of the change in optical refraction power $B_{COR}(r,\varphi)$ changes continuously from Ba to Bb in a transition area between $r_a$ and $r_b$, wherein $B_{COR}(r,\varphi)$ is a local change in optical refraction power in a plane lying in the vertex of the cornea and required for the desired correction of the defective vision.

9. The control data generating device according to claim 1, wherein the computer and the program together are configured to use $F=(1-1/n_c)\cdot\Delta z(r=0,\varphi)$ for the coefficient F, wherein $\Delta z(r=0, \varphi)$ is the central thickness of the subsurface volume to be isolated in the cornea and removed, wherein the computer and the program together are configured to iteratively calculate the optical refraction power $B^*_{CV}(r,\varphi)$, wherein the computer and the program together are configured to derive in each iteration step the central thickness $\Delta z(r=0, \varphi)$ of the subsurface volume from the difference between the central optical refraction powers $B^*_{CV}(r=0,\varphi)$ and $B_{CV}(r=0,\varphi)$, and apply this value when calculating $B^*_{CV}(r,\varphi)$ in a next iteration step.

10. A system for surgical correction of defective vision of an eye of a patient, the system comprising:

a laser system including a laser, a scanner and optics for emitting laser radiation to generate at least one cut in a cornea of the eye, and a control data generating device for generating control data for the laser system, the control data generating device comprising:

a computer operating under control of a program, the computer and the program together being configured to generate the control data to control the laser system to focus the laser radiation to different focus positions located within the cornea such that the at least one cut isolates a subsurface volume in the cornea, the subsequent removal of which subsurface volume from the cornea effects a desired correction of the defective vision; and the computer and the program together being configured to determine the control data by calculating an optical parameter of the cornea reduced by the subsurface volume;

wherein the optical parameter is locally varying and the optical parameter is either a radius of curvature $R^*_{CV}(r,\varphi)$ of the cornea reduced by the subsurface volume or an optical refraction power $B^*_{CV}(r,\varphi)$ the cornea has without the subsurface volume, wherein the optical parameter is the optical refraction power $B^*_{CV}(r,\varphi)$ the cornea has without the subsurface volume and wherein the computer and the program together are configured to calculate the optical refraction power $B^*_{CV}(r,\varphi)$ using the following equation;

$$B^*_{CV}(r,\varphi) = \frac{1}{\frac{1}{B_{CV}(r,\varphi) + B_{COR}(r,\varphi)} + \frac{F}{(n_C - 1)}}$$

wherein $B_{CV}(r,\varphi)$ is a local optical refraction power of cornea before the subsurface volume is removed, $n_c$ is the refractive index of the material of the cornea, F is a coefficient, and $B_{COR}(r,\varphi)$ is a local change in optical refraction power in a plane lying in the vertex of the cornea and required for the desired correction of the defective vision.

11. The system according to claim 10, wherein the laser system is adapted to shift a focus position along a path to generate the at least one cut within the cornea.

12. The system according to claim 10, wherein the optical parameter further comprises the radius of curvature $R^*_{CV}$ of the cornea reduced by the volume radius of curvature and wherein the radius of curvature $R^*_{CV}$ satisfies the following equation:

$R^*_{CV}(r,\varphi)=1/((1/R_{CV}(r,\varphi))+B_{COR}(r,\varphi)/(n_c-1))+F,$ wherein $R_{CV}(r,\varphi)$ is a local radius of curvature of the cornea before the subsurface volume is removed, $n_c$ is the refractive index of the material of the cornea, F is a coefficient, and $B_{COR}(r,\varphi)$ is a local change in optical refraction power in a plane lying in the vertex of the cornea and required for the desired correction of the defective vision.

13. The system according to claim 10, wherein, when determining the control data, the control data generating device defines at least two radii, r1 and r2, for which $B_{COR}(r=r1,\varphi) \#B_{COR}(r=r2,\varphi)$ holds true, wherein $B_{COR}(r,\varphi)$ is a local change in optical refraction power in a plane lying in the vertex of the cornea and required for the desired correction of the defective vision.

14. The system according to claim 10, wherein, when determining the control data, the computer and the program together are configured to define the local change in optical refraction power $B_{COR}(r,\varphi)$ such that there is a characteristic radius $r_{ch}$ for which a radial function of the change in optical refraction power $B_{COR}(r,\varphi)$ is piecewise constant, for which radii thus $B_{COR}(r<r_{ch},\varphi=\text{const})=B_a \neq B_b=B_{COR}(r>r_{ch},\varphi=\text{const})$ holds true, wherein $B_{COR}(r,\varphi)$ is a local change in optical refraction power in a plane lying in the vertex of the cornea and required for the desired correction of the defective vision.

15. The system according to claim 10, wherein, when determining the control data, the computer and the program together are configured to define the local change in optical refraction power $B_{COR}(r,\varphi)$ such that there are two radii $r_a$ and $r_b$ for which a radial function of change in optical refraction power $B_{COR}(r,\varphi)$ is piecewise constant, for which radii thus $B_{COR}(r<r_a,\varphi=\text{const})=B_a \neq B_b=B_{COR}(r>r_b,\varphi=\text{const})$ holds true, wherein the radial function of the change in optical refraction power $B_{COR}(r,\varphi)$ changes continuously from $B_a$ to $B_b$ in a transition area between $r_a$ and $r_b$, wherein $B_{COR}(r,\varphi)$ is a local change in optical refraction power in a plane lying in the vertex of the cornea and required for the desired correction of the defective vision.

16. The system according to claim 10, wherein the control data generating device uses $F=(1-1/n_c)\cdot\Delta z(r=0,\varphi)$ for the coefficient F, wherein $\Delta z(r=0,\varphi)$ is the central thickness of the subsurface volume to be isolated in the cornea and removed, and wherein the control data generating device iteratively calculates the radius of curvature $R^*_{CV}(r,\varphi)$, wherein the computer and the program together are configured to derive in each iteration step the central thickness $\Delta z(r=0,\varphi)$ of the subsurface volume from the difference between the central reciprocal radii of curvature $1/R^*_{CV}(r=0,\varphi)$ and $1/R_{CV}(r=0,\varphi)$, and to apply this value when calculating $R^*_{CV}(r,\varphi)$ in a next iteration step.

17. The system according to claim 10, wherein the control data generating device uses $F=(1-1/n_c)\cdot\Delta z(r=0,\varphi)$ for the coefficient F, wherein $\Delta z(r=0,\varphi)$ is the central thickness of the subsurface volume to be isolated in the cornea and removed, wherein the control data generating device iteratively calculates the optical refraction power $B^*_{CV}(r,\varphi)$, wherein the computer and the program together are configured to derive in each iteration step the central thickness $\Delta z(r=0,\varphi)$ of the subsurface volume from the difference between the central optical refraction powers $B^*_{CV}(r=0,\varphi)$ and $B_{CV}(r=0,\varphi)$, and to apply this value when calculating $B^*_{CV}(r,\varphi)$ in a next iteration step.

* * * * *

UNITED STATES PATENT AND TRADEMARK OFFICE
CERTIFICATE OF CORRECTION

| | | |
|---|---|---|
| PATENT NO. | : 12,076,275 B2 | Page 1 of 1 |
| APPLICATION NO. | : 17/091960 | |
| DATED | : September 3, 2024 | |
| INVENTOR(S) | : Gregor Stobrawa et al. | |

It is certified that error appears in the above-identified patent and that said Letters Patent is hereby corrected as shown below:

In the Claims

Column 26, Line 17, delete "Ich" and insert --$r_{CH}$--

Column 27, Line 48, delete "#" and insert --$\neq$--

Signed and Sealed this
Third Day of December, 2024

Katherine Kelly Vidal
*Director of the United States Patent and Trademark Office*